US005854044A

United States Patent [19]
Pastan et al.

[11] Patent Number: 5,854,044
[45] Date of Patent: Dec. 29, 1998

[54] RECOMBINANT PSEUDOMONAS EXOTOXIN WITH INCREASED ACTIVITY

[75] Inventors: Ira H. Pastan, Potomac; David J. Fitzgerald, Silver Springs, both of Md.

[73] Assignee: National Institutes of Health, Bethesda, Md.

[21] Appl. No.: 463,480

[22] Filed: Jun. 5, 1995

Related U.S. Application Data

[62] Division of Ser. No. 405,615, Mar. 15, 1995, Pat. No. 5,602,095, which is a continuation of Ser. No. 901,709, Jun. 18, 1992, abandoned.

[51] Int. Cl.⁶ .............................. C07K 19/00; C12N 9/12
[52] U.S. Cl. ........................ 435/194; 530/324; 530/350; 530/351; 530/387.7; 530/387.3; 530/399
[58] Field of Search ........................ 435/194; 530/324.1, 530/350, 399, 351, 387.7, 387.3

[56] References Cited

U.S. PATENT DOCUMENTS

| 4,892,827 | 1/1990 | Pastan et al. | 435/193 |
|---|---|---|---|
| 5,082,927 | 1/1992 | Pastan et al. | 530/350 |

FOREIGN PATENT DOCUMENTS

WO 91/18099  11/1991  WIPO.

OTHER PUBLICATIONS

Chaudhary et al., *Proc. Natl. Acad. Sci. USA*, 84:4538–4542 (1987).

Chaudhary et al., *Proc. Natl. Acad. Sci. USA*, 85:2939–2943 (1988).

Siegall, C.B. et al., "Functional Analysis of Domains II, Ib, and III of Pseudomonas Exotoxin", *Journal of Biological Chemistry*, 264:14256–14261 (1989).

Lorberboum–Galski, H. et al., "IL2–PE66⁴ᴳˡᵘ, a New Chimeric Protein cytotoxic to Human–activated T Lymphocytes", *Journal of Biological Chemistry*, 265:16311–16317 (1990).

Heimbrook, D.C. et al., "Transforming growth factor α–Pseudomonas exotoxin fusion protein prolongs survival of nude mice bearing tumor xenografts", *Proc. Natl. Acad. Sci. USA*, 87:4697–4701 (1990).

Chaudhary et al., *Proc. Natl. Acad. Sci. USA*, 87:308–312 (1990).

Seetharam, S. et al., "Increased Cytotoxic Activity of Pseudomonas Exotoxin and Two Chimeric Toxins Ending in KDEL", *Journal of Biological Chemistry*, 266:17376–17381 (1991).

Kreitman, R.J. et al., "Properties of Chimeric Toxins with Two Recognition Domains: Interleukin 6 and Transforming Growth Factor α at Different Locations in Pseudomonas Exotoxin", *Bioconjugate Chemistry*, pp. 63–68 (1992).

Kreitman, R.J. et al., "Rational Design of a Chimeric Toxin: An Intramolecular Location for the Insertion of Transforming Growth Factor α within Pseudomonas Exotoxin as a Targeting Ligand", *Bioconjugate Chemistry*, pp. 58–62 (1992).

Siegall et al., 1991, *Biochem.* 30,7154–7159.

Gray et al., 1984 *Proc. Nat'l. Acad. Sci. USA* 81, 2645–2649.

Ogata et al., 1990 *J. Biol. Chem.* 265, 20678–20685.

Jinno et al., 1989 *J. Biol. Chem.* 264, 15953–15959.

Pastan et al., *Science* 254:1173–1177 (1991).

Theuer et al., *J. Biol. Chem.* 267:16872–16877 (1992).

*Primary Examiner*—Rebecca E. Prouty
*Attorney, Agent, or Firm*—Townsend and Townsend and Crew LLP

[57] ABSTRACT

This invention relates to the production and use of recombinant Pseudomonas-derived toxins modified to increase their toxicity and potency in therapy. More particularly, the invention relates to certain deletions in domain II of the amino acid sequence of Pseudomonas exotoxin the domain which relates to the toxin's natural proteolytic processing.

13 Claims, 8 Drawing Sheets

43 kD                68 kD

PE280-313, 380-613/TGFα

PE287-613/TGFα

PE284-613/TGFα

PE282-613/TGFα

PE280-613/TGFα

PE280-613

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 613 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( x i ) SEQUENCE DESCRIPTION: SEQ ID NO:1:

```
Ala Glu Glu Ala Phe Asp Leu Trp Asn Glu Cys Ala Lys Ala Cys Val
 1               5                  10                  15
Leu Asp Leu Lys Asp Gly Val Arg Ser Ser Arg Met Ser Val Asp Pro
             20                  25                  30
Ala Ile Ala Asp Thr Asn Gly Gln Gly Val Leu His Tyr Ser Met Val
         35                  40                  45
Leu Glu Gly Gly Asn Asp Ala Leu Lys Leu Ala Ile Asp Asn Ala Leu
     50                  55                  60
Ser Ile Thr Ser Asp Gly Leu Thr Ile Arg Leu Glu Gly Gly Val Glu
 65                  70                  75                  80
Pro Asn Lys Pro Val Arg Tyr Ser Tyr Thr Arg Gln Ala Arg Gly Ser
                 85                  90                  95
Trp Ser Leu Asn Trp Leu Val Pro Ile Gly His Glu Lys Pro Ser Asn
             100                 105                 110
Ile Lys Val Phe Ile His Glu Leu Asn Ala Gly Asn Gln Leu Ser His
         115                 120                 125
Met Ser Pro Ile Tyr Thr Ile Glu Met Gly Asp Glu Leu Leu Ala Lys
     130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                 165                 170                 175
Ala Gln Thr Gln Pro Arg Arg Glu Lys Arg Trp Ser Glu Trp Ala Ser
             180                 185                 190
Gly Lys Val Leu Cys Leu Leu Asp Pro Leu Asp Gly Val Tyr Asn Tyr
         195                 200                 205
Leu Ala Gln Gln Arg Cys Asn Leu Asp Asp Thr Trp Glu Gly Lys Ile
     210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
                 245                 250                 255
Ala Ala Leu Thr Ala His Gln Ala Cys His Leu Pro Leu Glu Thr Phe
             260                 265                 270
Thr Arg His Arg Gln Pro Arg Gly Trp Glu Gln Leu Glu Gln Cys Gly
         275                 280                 285
Tyr Pro Val Gln Arg Leu Val Ala Leu Tyr Leu Ala Ala Arg Leu Ser
     290                 295                 300
Trp Asn Gln Val Asp Gln Val Ile Arg Asn Ala Leu Ala Ser Pro Gly
```

|     |     |     |     | 305 |     |     |     |     | 310 |     |     |     |     | 315 |     |     |     |     | 320 |
|-----|-----|-----|-----|-----|-----|-----|-----|-----|-----|-----|-----|-----|-----|-----|-----|-----|-----|-----|-----|
| Ser | Gly | Gly | Asp | Leu | Gly | Glu | Ala | Ile | Arg | Glu | Gln | Pro | Glu | Gln | Ala |
|     |     |     |     | 325 |     |     |     |     | 330 |     |     |     |     | 335 |     |
| Arg | Leu | Ala | Leu | Thr | Leu | Ala | Ala | Ala | Glu | Ser | Glu | Arg | Phe | Val | Arg |
|     |     |     |     | 340 |     |     |     |     | 345 |     |     |     |     | 350 |     |
| Gln | Gly | Thr | Gly | Asn | Asp | Glu | Ala | Gly | Ala | Ala | Asn | Ala | Asp | Val | Val |
|     |     |     |     | 355 |     |     |     |     | 360 |     |     |     |     | 365 |     |
| Ser | Leu | Thr | Cys | Pro | Val | Ala | Ala | Gly | Glu | Cys | Ala | Gly | Pro | Ala | Asp |
|     |     |     |     | 370 |     |     |     |     | 375 |     |     |     |     | 380 |     |
| Ser | Gly | Asp | Ala | Leu | Leu | Glu | Arg | Asn | Tyr | Pro | Thr | Gly | Ala | Glu | Phe |
|     |     |     |     | 385 |     |     |     |     | 390 |     |     |     |     | 395 |     | 400 |
| Leu | Gly | Asp | Gly | Gly | Asp | Val | Ser | Phe | Ser | Thr | Arg | Gly | Thr | Gln | Asn |
|     |     |     |     |     |     | 405 |     |     |     |     | 410 |     |     |     |     | 415 |
| Trp | Thr | Val | Glu | Arg | Leu | Leu | Gln | Ala | His | Arg | Gln | Leu | Glu | Glu | Arg |
|     |     |     |     | 420 |     |     |     |     | 425 |     |     |     |     | 430 |     |
| Gly | Tyr | Val | Phe | Val | Gly | Tyr | His | Gly | Thr | Phe | Leu | Glu | Ala | Ala | Gln |
|     |     |     |     | 435 |     |     |     |     | 440 |     |     |     |     | 445 |     |
| Ser | Ile | Val | Phe | Gly | Gly | Val | Arg | Ala | Arg | Ser | Gln | Asp | Leu | Asp | Ala |
|     |     |     |     | 450 |     |     |     |     | 455 |     |     |     |     | 460 |     |
| Ile | Trp | Arg | Gly | Phe | Tyr | Ile | Ala | Gly | Asp | Pro | Ala | Leu | Ala | Tyr | Gly |
|     |     |     |     | 465 |     |     |     |     | 470 |     |     |     |     | 475 |     | 480 |
| Tyr | Ala | Gln | Asp | Gln | Glu | Pro | Asp | Ala | Arg | Gly | Arg | Ile | Arg | Asn | Gly |
|     |     |     |     |     |     | 485 |     |     |     |     | 490 |     |     |     |     | 495 |
| Ala | Leu | Leu | Arg | Val | Tyr | Val | Pro | Arg | Ser | Ser | Leu | Pro | Gly | Phe | Tyr |
|     |     |     |     | 500 |     |     |     |     | 505 |     |     |     |     | 510 |     |
| Arg | Thr | Ser | Leu | Thr | Leu | Ala | Ala | Pro | Glu | Ala | Ala | Gly | Glu | Val | Glu |
|     |     |     |     | 515 |     |     |     |     | 520 |     |     |     |     | 525 |     |
| Arg | Leu | Ile | Gly | His | Pro | Leu | Pro | Leu | Arg | Leu | Asp | Ala | Ile | Thr | Gly |
|     |     |     |     | 530 |     |     |     |     | 535 |     |     |     |     | 540 |     |
| Pro | Glu | Glu | Glu | Gly | Gly | Arg | Leu | Glu | Thr | Ile | Leu | Gly | Trp | Pro | Leu |
|     |     |     |     | 545 |     |     |     |     | 550 |     |     |     |     | 555 |     | 560 |
| Ala | Glu | Arg | Thr | Val | Val | Ile | Pro | Ser | Ala | Ile | Pro | Thr | Asp | Pro | Arg |
|     |     |     |     |     |     | 565 |     |     |     |     | 570 |     |     |     |     | 575 |
| Asn | Val | Gly | Gly | Asp | Leu | Asp | Pro | Ser | Ser | Ile | Pro | Asp | Lys | Glu | Gln |
|     |     |     |     |     |     | 580 |     |     |     |     | 585 |     |     |     |     | 590 |
| Ala | Ile | Ser | Ala | Leu | Pro | Asp | Tyr | Ala | Ser | Gln | Pro | Gly | Lys | Pro | Pro |
|     |     |     |     | 595 |     |     |     |     | 600 |     |     |     |     | 605 |     |
| Arg | Glu | Asp | Leu | Lys |
|     |     |     |     | 610 |

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (primer)

( i i i ) HYPOTHETICAL: NO ( x i ) SEQUENCE DESCRIPTION: SEQ ID NO:2:

ATGTGGGAAC AACTCGAGCA TATGGGCTAT CCGGTGCAG    39

( 2 ) INFORMATION FOR SEQ ID NO:3:

( i ) SEQUENCE CHARACTERISTICS:

-continued (A) LENGTH: 30 base pairs
    (B) TYPE: nucleic acid
    (C) STRANDEDNESS: single
    (D) TOPOLOGY: linear (ii) MOLECULE TYPE: DNA (primer)

(iii) HYPOTHETICAL: NO (xi) SEQUENCE DESCRIPTION: SEQ ID NO:3:

GGGCACCGTT GCGGATCCGG CCGCGTGCGT                    30

(2) INFORMATION FOR SEQ ID NO:4:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: DNA (primer)

(iii) HYPOTHETICAL: NO (xi) SEQUENCE DESCRIPTION: SEQ ID NO:4:

GATATACAAA TGCATATGCA ACTCGAGCAG AGCGGCTATC CGGTG       45

(2) INFORMATION FOR SEQ ID NO:5:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: DNA (primer)

(iii) HYPOTHETICAL: NO (xi) SEQUENCE DESCRIPTION: SEQ ID NO:5:

CAAATGTGGG AACATATGGA GCAGAGCGGC TATCCGGTG           39

(2) INFORMATION FOR SEQ ID NO:6:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (ii) MOLECULE TYPE: DNA (primer)

(iii) HYPOTHETICAL: NO (xi) SEQUENCE DESCRIPTION: SEQ ID NO:6:

GAAGGAGATA TACATATGTG GGAACAAGAG CAGTGCGG             38

(2) INFORMATION FOR SEQ ID NO:7:

(i) SEQUENCE CHARACTERISTICS:
    (A) LENGTH: 86 base pairs
    (B) TYPE: nucleic acid
    (C) STRANDEDNESS: single
    (D) TOPOLOGY: linear (ii) MOLECULE TYPE: DNA (primer)

(iii) HYPOTHETICAL: NO (xi) SEQUENCE DESCRIPTION: SEQ ID NO:7:

TATGTGGGAA CAACTCGAGC AGAGCGGCTA TCCGGTGCAG CGACTAGTAG CGCTCTACCT    60

GGCGGCGCGG CTGTCGTGGA ACCAGG                                                86

(2) INFORMATION FOR SEQ ID NO:8:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (primer)

(iii) HYPOTHETICAL: NO (xi) SEQUENCE DESCRIPTION: SEQ ID NO:8:

TCGACCTGGT TCCACGACAG CCGCGCCAGG TAGAGCGCTA CTAGTCGCTG CACCGGATAG    60

CCGCTCTCGA GTTGTTCCCA CC                                              82

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)

(iii) HYPOTHETICAL: NO (xi) SEQUENCE DESCRIPTION: SEQ ID NO:9:

TCGACCAGGT GATCCGCGGC C                                               21

(2) INFORMATION FOR SEQ ID NO:10:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (primer)

(iii) HYPOTHETICAL: NO (xi) SEQUENCE DESCRIPTION: SEQ ID NO:10:

GGTCCACTAG GCG                                                        13

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (oligonucleotide duplex)

(iii) HYPOTHETICAL: NO (ix) FEATURE:
        (A) NAME/KEY: misc_feature
        (B) LOCATION: 3..21
        (D) OTHER INFORMATION: /note= "complementary strand begins
            at position 3 and concludes with
            TT overhang"

(xi) SEQUENCE DESCRIPTION: SEQ ID NO:11:

TATGCTGCAG GGTACCAAGC T                                               21

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:12:

Met Trp Glu Gln Leu Glu Gln Ser Gln Tyr Pro Val Gln Arg
    1                5                      10

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:13:

Met Trp Glu Gln Leu Glu Gln
    1                5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:14:

Arg Glu Asp Leu Lys
    1                5

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:15:

Arg Glu Asp Leu
    1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear (i i) MOLECULE TYPE: peptide (i i i) HYPOTHETICAL: NO (x i) SEQUENCE DESCRIPTION: SEQ ID NO:16:

Lys Asp Glu Leu
1

RECOMBINANT PSEUDOMONAS EXOTOXIN WITH INCREASED ACTIVITY

This is a Division of application Ser. No. 08/405,615, filed Mar. 15, 1995 now U.S. Pat No. 5,602,095, which was a continuation of application Ser. No. 07/901,709, filed Jun. 18, 1992, now abandoned.

This invention relates to the production and use of recombinant Pseudomonas-derived toxins modified to increase their toxicity and potency in therapy. More particularly, the invention relates to exotoxins comprising deletions in the amino acid sequence that represent the removal of domain Ia and certain sequences of domain II of Pseudomonas exotoxin.

BACKGROUND OF THE INVENTION

Toxins attached to growth factors, antibodies and other cell targeting molecules can be used to kill harmful cells bearing specific receptors or antigens (Pastan et al., *Cell* 47:641 (1986) and Vitetta et al, *Science* 238:1098 (1987)). One promising source for an effective therapeutic toxin is Pseudomonas exotoxin A. Pseudomonas exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes death. The function of domain Ib (amino acids 365–399) remains undefined, although a large part of it, amino acids 365–380, can be deleted without loss of cytotoxicity. See Siegall et al., *Biochem.* 30:7154–7159 (1991). PE has been combined with growth factors, antibodies or CD4 to create toxins that can be selectively targeted to cells with different cell membrane proteins as reviewed in Pastan and FitzGerald, *Science* 254:1173–1177 (1991).

Native PE characteristically produces death due to liver failure. Immunotoxins with PE also attack the liver and, when given in much larger (20 to 250-fold larger) doses, may produce death due to liver toxicity. Improved forms of PE that reduce non-specific toxicity in the host and which improve therapeutic efficacy are highly desirable. Variants of PE omitting the cell binding domain Ia have been found to be effective while reducing the amount of non-specific toxicity. See, U.S. Pat. No. 4,892,827, for example.

SUMMARY OF THE INVENTION

This invention discloses improved recombinant Pseudomonas exotoxin molecules that demonstrate higher activities than prior described molecules. Further, the discoveries described here enable one to create PE molecules that are smaller in size, likely to be less immunogenic, that are able to enter the cytosol of target cells, and better able to penetrate the interior of tumors.

To be cytotoxic native PE must be proteolytically cleaved within cells (Ogata et al., *J. Biol Chem.* 265:20678–20685 (1990)). This cleavage takes place between amino acid 279 and 280. The importance of the cleavage is illustrated with results that indicate that mutant forms of PE that cannot be cleaved at this site are non-toxic. Ogata et al., supra. However, cleavage by cells is not very efficient. The present invention aims to overcome the problem of inefficient cleavage by constructing a PE derivative that requires no cleavage by cells. Such "pre-cleaved" PE molecules have increased potency because the efficiency of delivery of active toxin fragments to the cytosol is increased.

The invention includes recombinant Pseudomonas exotoxin molecules in which domain Ia is deleted and no more than the first 27 amino acids from the amino terminal end of domain II have been deleted. A preferred PE molecule begins with a methionine at amino acid position 280 of domain II, comprises the deletion of about amino acids 365 to 380 of domain Ib and includes a substitution of serine at amino acid position 287 in place of cysteine. Preferred molecules also include those that have an amino acid sequence at a carboxyl terminal end of the molecule selected from the group consisting of REDLK (Seq. ID No. 14), REDL (Seq. ID No. 15), and KDEL (Seq. ID No. 16). Exemplary PE molecules may consist essentially of about amino acids 280 to 613 or consist essentially of about amino acids 280 to 364 and 381 to 613.

The PE molecules may also be fused to ligand binding agents such as antibodies or binding fragments thereof, growth factors, hormones, cytokines and the like. The ligand binding agent is preferably inserted after about amino acid position 607 and amino acids 604–613 are placed at the C-terminus of the ligand. Because we have shown that only certain sequences in domain II are necessary to translocate a binding protein into the cytosol of a cell, the PE molecules of this invention may be used to transport various peptides into cells. Domain III may be deleted from PE molecules and replaced with other peptides for use as a vaccine or in gene therapeutic applications.

The PE molecules are also characterized by having a deletion of domain Ia and a deletion in the amino terminal end of domain II such that the molecule is at least twenty times more cytotoxic to target cells than PE40 (described below) in a cytotoxicity assay wherein the cytotoxicity to the target cells of PE40 and the recombinant PE molecule described herein is measured by assaying against the target cells, PE40 fused to a ligand binding agent specific for the target cells and the recombinant PE molecule fused to a ligand binding agent specific for the target cells.

Vectors comprising a nucleic acid sequence encoding the amino acid sequences of the PE molecules and host cells expressing the molecules are also contemplated. Further included are pharmaceutical compositions and methods for treating cancer and other conditions with the novel molecules described here.

DETAILED DESCRIPTION

Figure 1:
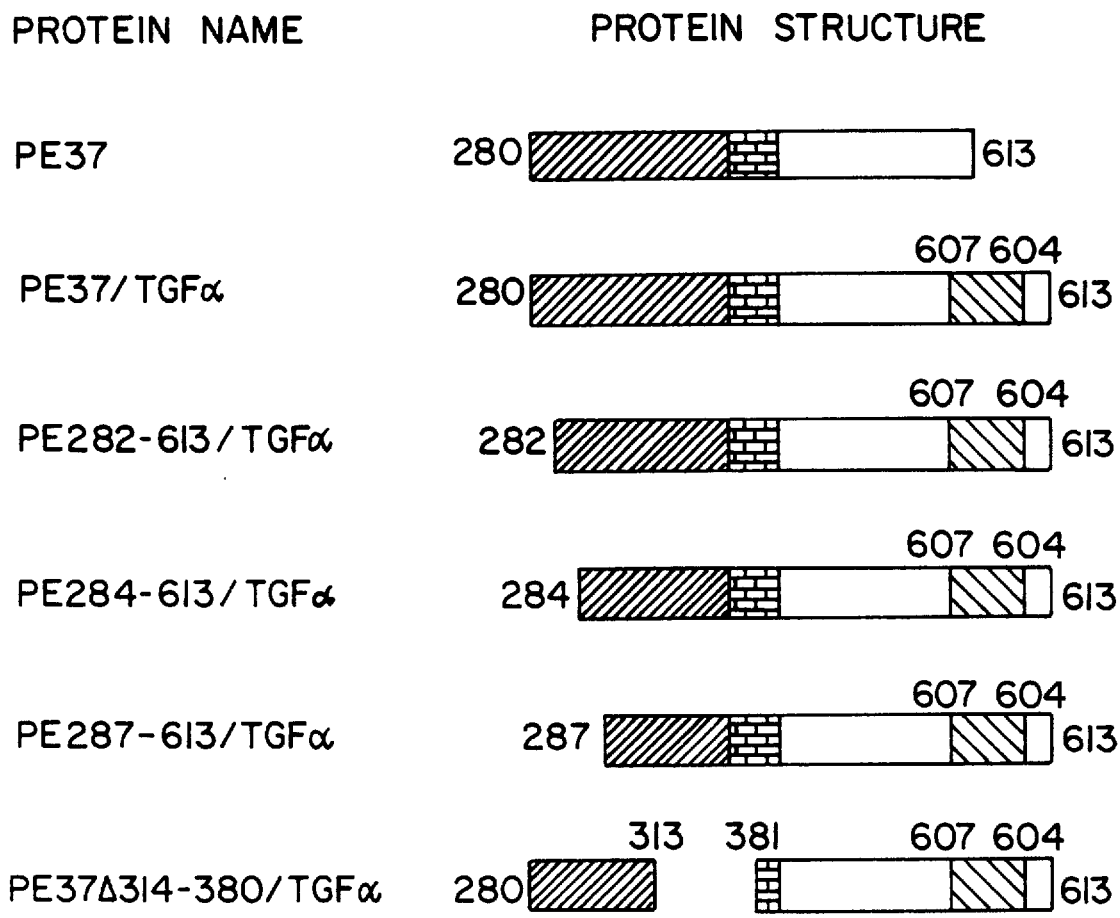
FIG. 1 is a schematic of expressed proteins representing certain deletions in domain II of PE. In addition, all amino acids of domain Ia have deleted. The positions of amino acids that span PE sequences are numbered.
Figure 2:
FIG. 2 is a SDS-PAGE of expressed proteins depicted in FIG. 1. The 10.0% protein gel is stained with Coomassie Blue. Molecular masses of the standards are indicated at the left margin.
Figure 2:
Figure 2:
Figure 2:
Figure 2:
Figure 2:
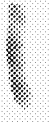
Figure 3:
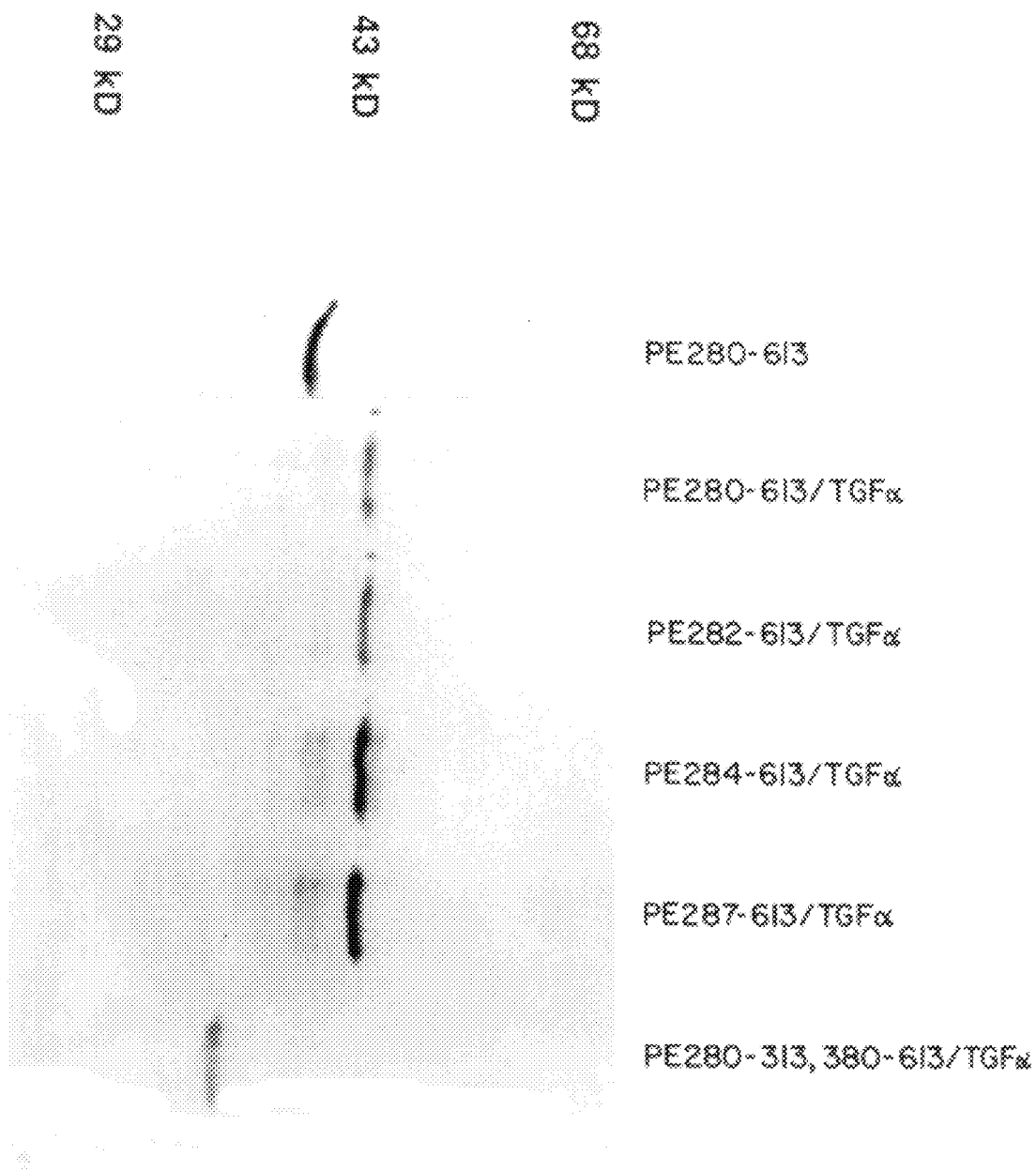
FIG. 3 is an immunoblot analysis of expressed proteins depicted in FIG. 1 Pseudomonas exotoxin. Molecular masses of the standards are indicated at the left margin.
Figure 4A:
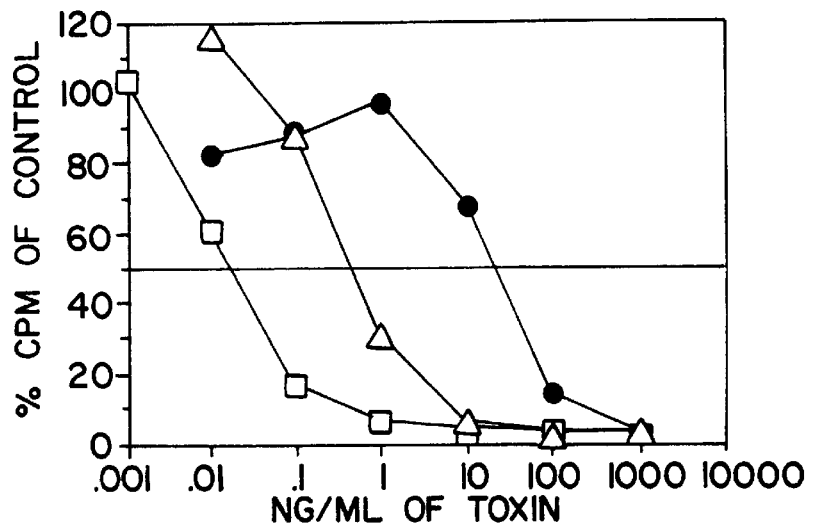
FIG. 4A and 4B show protein synthesis inhibition of A431 cells by PE37/T (open square), PE(4E)/T (open triangle), and PE37Δ314-380/T (closed circle) at left (FIG. 4A) and PE37/T (open square), PE282-613/T (closed triangle), PE284-613/T (closed square) and PE287-613/T (open circle) at right (FIG. 4B). [³H]leucine incorporation is expressed as the percentage of cpm of cells incubated without toxin.
Figure 4B:
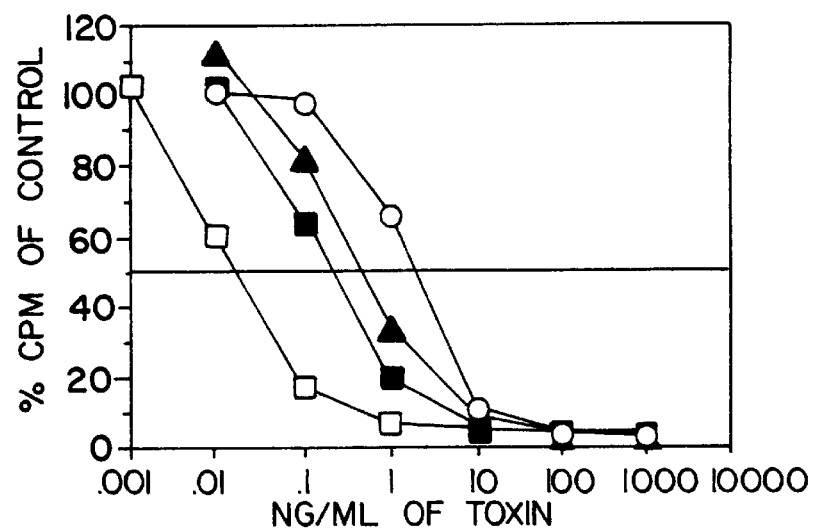
Figure 5:
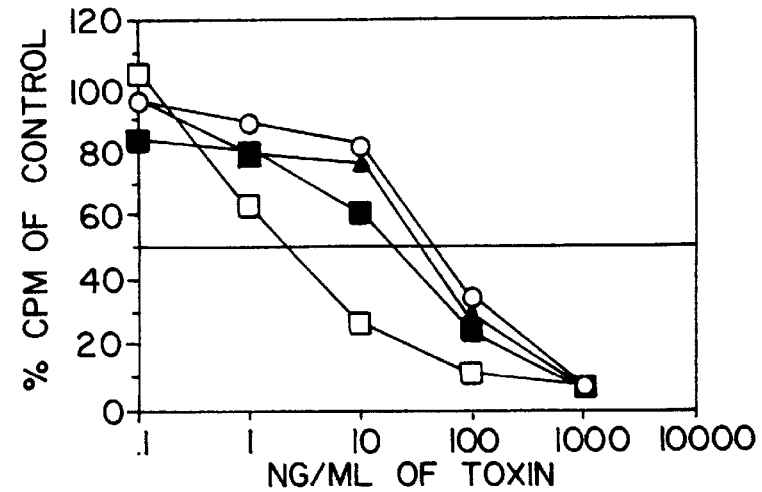
FIG. 5 shows protein synthesis inhibition of MCF-7 cells by PE37/T (open square), PE282-613/T (closed triangle), PE284-613 (closed square) and PE287-613/T (open circle). [³H]leucine incorporation is expressed as the percentage of cpm of cells incubated without toxin.
Figure 6A:
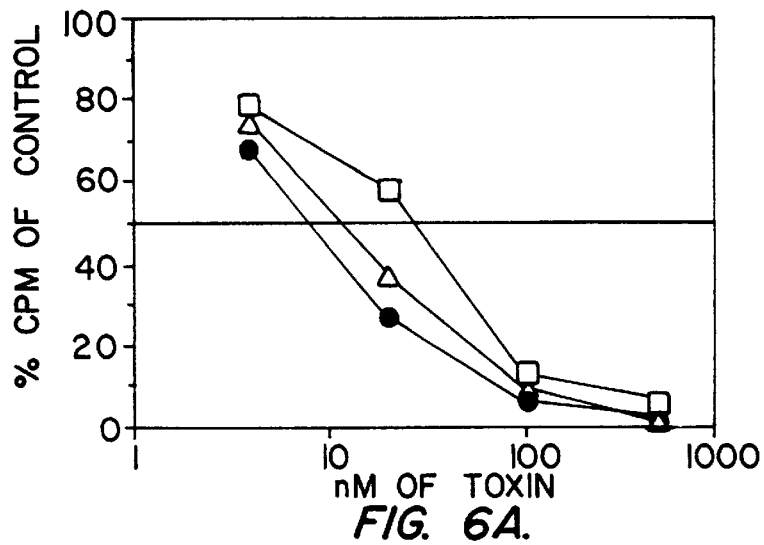
FIG. 6A and 6B show displacement of [$^{125}$I]-EGF from A431 cells by PE37/T (open square), PE(4E)/T (open triangle) and PE37Δ314-380/T (closed circle) at left (FIG. 6A) and PE37/T (open square), PE282-613/T (closed triangle), PE284-613 (closed square) and PE287-613/T (open circle) at right (FIG. 6B). [$^{125}$I]-EGF bound to A431 cells was measured as dpm and expressed as the percentage of dpm of cells incubated without toxin.
Figure 6B:
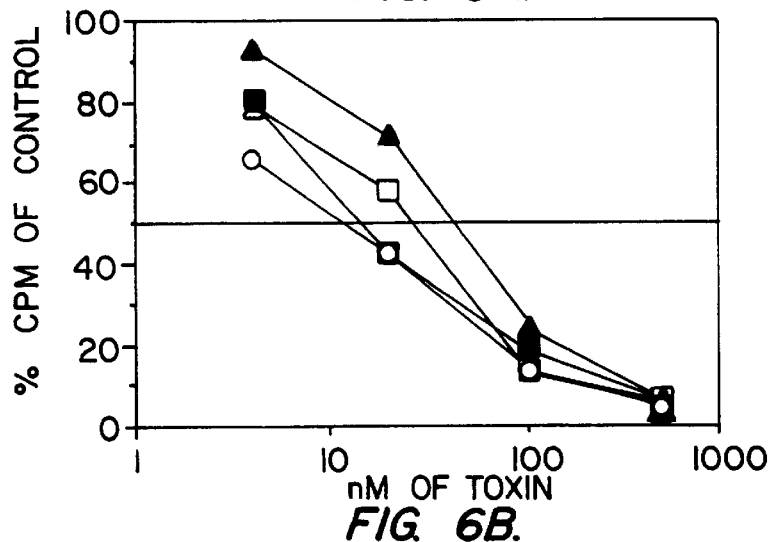
Figure 8:
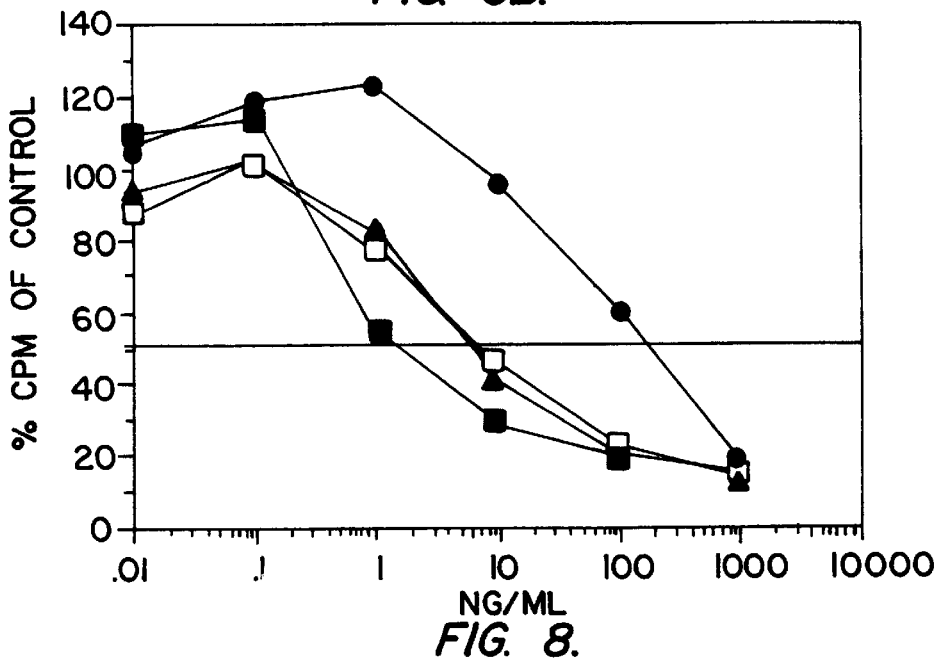
FIG. 8: Protein synthesis inhibition activity of HB21 conjugates on A431 cells: HB21-S-C-PE35(closed circle), HB21-S-C-PE38(closed triangle), HB21-S-S-PE38(open square), and HB21-S-S-PE35(closed square).
Figure 7A:
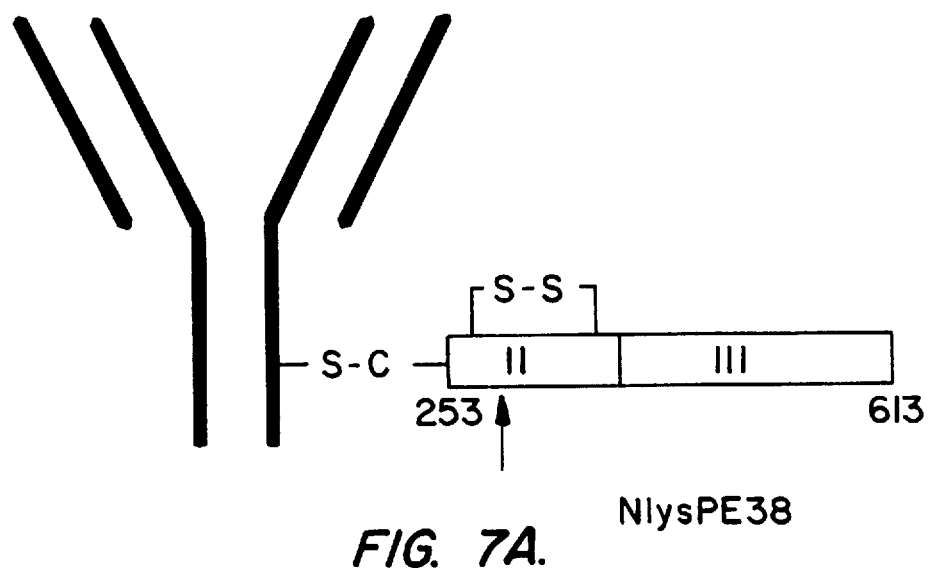
FIG. 7A and 7B. A: schematic diagram of an immunotoxin containing MAb conjugated by a thioether bond to lysPE38. Also pictured is the disulfide bond spanning residues 265 and 287 of domain II. The arrow indicates the site of proteolytic cleavage required to generate the 37 kD fragment that translocates to the cytosol. B: Schematic diagram of an immunotoxin containing MAb conjugated by a disulfide bond to PE35 through a cysteine residue at position 287. Reduction of the disulfide bond inside cells generates a toxin fragment able to translocate to the cytosol.
Figure 7B:
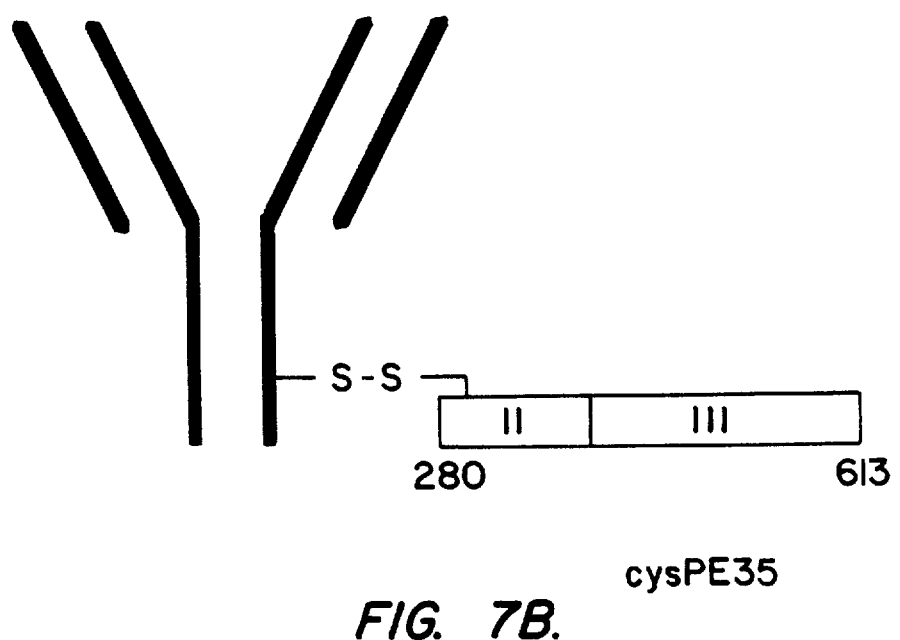

This invention relates to recombinant Pseudomonas exotoxin molecules having increased cytotoxic activity in which a portion of the amino terminal end of domain II has been deleted. This molecule may be linked or fused to other target molecules so that the improved cytotoxin is targeted to desired cells.

Native PE has the amino acid sequence set forth in Sequence ID Listing No. 1. All amino acid sequence positions described herein use as a frame of reference this sequence listing. For example, a PE molecule "consisting essentially of about amino acids 280 to 613" would refer to a molecule having amino acids substantially corresponding to those positions on Sequence ID Listing No. 1. Other common references are used herein to indicate deletions or substitutions to a sequence using Sequence ID Listing No. 1 as the frame of reference. The use of the symbol "Δ" refers to a deletion of the amino acids following the symbol. For example, "Δ365–380", refers to the deletion from a PE molecule of amino acids 365 to 380. Amino acid substitutions may be indicated by parentheses, for example "(ser 287)" refers to a molecule having serine at amino acid position 287. Amino acids are also sometimes referred to here by the single letter codes recommended by the IUPAC-IUB Biochemical Nomenclature Commission.

Many of the PE molecules of this invention are uniquely characterized by their increased cytotoxicity to target cells when coupled with a ligand binding agent specific for the target cells. The increased cytotoxicity occurs in comparison to the use of native PE molecules or those where no significant deletion of domain II has occurred, such as PE(4E) or PE40 described in the Example section below and commonly assigned U.S. Ser. No. 07/459,635 and U.S. Ser. No. 07/522,182, both of which are incorporated by reference. An assay for determining an increase in cytotoxicity is one where a fusion protein comprising the subject PE molecule and a ligand binding agent is compared with a fusion protein comprising the reference PE molecule, e.g. PE40, and the same ligand binding agent. The respective fusion proteins are then tested in cytotoxicity assays against cells specific for the ligand binding agent. ID$_{50}$s (defined below) obtained may be adjusted to obtain a cytotoxicity index by adjusting the values such that the concentration of toxin that displaces 50% of labeled ligand from ligand receptors is divided by the ID$_{50}$ of the recombinant toxin on cells bearing the ligand receptors. The cytotoxicity index for each PE molecule is then compared. An exemplary assay is set forth in the Examples provided below using TGFα as the ligand binding agent and A431 cells bearing the EGF receptor. PE molecules having corrected cytotoxicity indexes of about 20 times or more, preferably about 60 times or more, and most preferably about 300 times or more, over PE40 or other PE molecules where no deletion of domain II has occurred are desired. A PE molecule lacking domain Ia may be expressed by plasmid pJH8 which expresses domains II, Ib and III. Plasmid pJH8 is described in U.S. Pat. No. 4,892,827 incorporated by reference herein and is available from the American Type Culture Collection in Rockville, Md. as ATCC 67208.

"ID$_{50}$" refers to the concentration of the toxin that inhibits protein synthesis in the target cells by 50%, which is typically measured by standard ³H-leucine incorporation assays. Displacement assays or competitive binding assays are well known and described in the art. They measure the ability of one peptide to compete with another peptide for the binding of a target antigen.

A preferred PE molecule is one in which domain Ia is deleted and no more than the first 27 amino acids have been deleted from the amino terminal end of domain II. This substantially represents the deletion of amino acids 1 to 279. The cytotoxic advantage created by this deletion is greatly decreased if the following deletions are made: 1–281; 1–283; 1–286; and 314–380. It is surprising that the deletion of 27, but not 29, 31, 33 or 36 amino acids from the amino end of domain II results in increased toxic activity since this domain is responsible for the translocation of the toxin into the cytosol.

In addition, the PE molecules can be further modified using site-directed mutagenesis or other techniques known in the art, to alter the molecule for particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (as in native PE), REDL or KDEL, repeats of those, or other sequences that function to maintain or recycle proteins into the endoplasmic reticulum, referred to here as "endoplasmic retention sequences". See, for example, Chaudhary et al, Proc. Natl. Acad. Sci. USA 87:308–312 and Seetharam et al, J. Biol. Chem. 266: 17376–17381 (1991) and commonly assigned, U.S. Ser. No. 07/459,635 filed Jan. 2, 1990, all of which are incorporated by reference herein.

Deletions of amino acids 365–380 of domain Ib can be made without loss of activity. Further, a substitution of methionine at amino acid position 280 in place of glycine to allow the synthesis of the protein to begin and of serine at amino acid position 287 in place of cysteine to prevent formation of improper disulfide bonds is beneficial.

A "ligand binding agent" refers generally to all molecules capable of reacting with or otherwise recognizing or binding to a receptor on a target cell. Examples of such binding agents include, but are not limited to, antibodies, growth factors such as TGFα, IL2, IL4, IL6, IGF1 or CD4, lymphokines, cytokines, hormones and the like which specifically bind desired target cells.

The term "antibody" includes various forms of modified or altered antibodies, such as an intact immunoglobulin, an Fv fragment containing only the light and heavy chain variable regions, a Fab or (Fab)'$_2$ fragment containing the variable regions and parts of the constant regions, a single-chain antibody (Bird et al., Science 242, 424–426 (1988); Huston et al., Proc. Nat. Acad. Sci. USA 85, 5879–5883 (1988)), and the like. The antibody may be of animal (especially mouse or rat) or human origin or may be chimeric (Morrison et al., Proc Nat. Acad. Sci. USA 81, 6851–6855 (1984)) or humanized (Jones et al., Nature 321, 522–525 (1986), and published UK patent application #8707252). Methods of producing antibodies suitable for use in the present invention are well known to those skilled in the art and can be found described in such publications as Harlow & Lane, Antibodies: A Laboratory Manual, Cold Spring Harbor Laboratory, (1988).

The recombinant PE molecules of the present invention may be fused to, or otherwise bound to a ligand binding agent by any method known and available to those in the art. The two components may be chemically bonded together by any of a variety of well-known chemical procedures. For example, the linkage may be by way of heterobifunctional cross-linkers, e.g. SPDP, carbodiimide, glutaraldehyde, or the like. Production of various immunotoxins is well-known within the art and can be found, for example in "Monoclonal Antibody-Toxin Conjugates: Aiming the Magic Bullet," Thorpe et al., Monoclonal Antibodies in Clinical Medicine, Academic Press, pp. 168–190 (1982) and Waldmann, Science, 252:1657 (1991), both of which are incorporated by reference. To use the recombinant PE molecules with an antibody, a form of the PE molecule with cysteine at amino acid position 287 is preferred to couple the toxin to the antibody or other ligand through the thiol moiety of cysteine.

The PE molecules may also be fused to the ligand binding agent by recombinant means such as through the production of single chain antibodies in E. coli. The genes encoding protein chains may be cloned in cDNA or in genomic form by any cloning procedure known to those skilled in the art. See for example Sambrook et al., Molecular Cloning: A Laboratory Manual, Cold Spring Harbor laboratory, (1989).

It is desirable to insert the ligand binding agent at a point within domain III of the PE molecule, particularly for smaller agents such as TGFA (transforming growth factor α). Most preferably the ligand binding agent is fused between about amino acid positions 607 and 604 of the PE molecule. This means that the ligand binding agent is inserted after about amino acid 607 of the molecule and an appropriate carboxyl end of PE is recreated by placing amino acids about 604–613 of PE after the binding agent. Thus, the ligand binding agent is inserted within the recombinant PE molecule after about amino acid 607 and is followed by amino acids 604– 613 of domain III. $V_L$ and $V_H$ regions from a desired antibody may also be inserted in a single chain form within domain III.

Binding agents may also be inserted in replacement for domain Ia as has been accomplished in what is known as the TGFα/PE40 molecule (also referred to as TP40) described in Heimbrook et al., Proc. Natl. Acad. Sci., USA, 87:4697–4701 (1990) and in commonly assigned U.S. Ser. No. 07/865,722 filed Apr. 8, 1992 and in U.S. Ser. No. 07/522,563 filed May 14, 1990, all of which are incorporated by reference.

Those skilled in the art will realize that additional modifications, deletions, insertions and the like may be made to the ligand binding agent and PE genes. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

Fusion proteins of the invention including PE molecules may be expressed in a variety of host cells, including E. coli, other bacterial hosts, yeast, and various higher eucaryotic cells such as the COS, CHO and HeLa cells lines and myeloma cell lines. The recombinant protein gene will be operably linked to appropriate expression control sequences for each host. For E. coli this includes a promoter such as the T7, trp, or lambda promoters, a ribosome binding site and preferably a transcription termination signal. For eucaryotic cells, the control sequences will include a promoter and preferably an enhancer derived from immunoglobulin genes, SV40, cytomegalovirus, etc., and a polyadenylation sequence, and may include splice donor and acceptor sequences. The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, Protein Purification, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

The recombinant fusion proteins and pharmaceutical compositions of this invention are particularly useful for parenteral administration, such as intravenous administration or administration into a body cavity or lumen of an organ. The compositions for administration will commonly comprise a solution of the PE molecule fusion protein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the recombinant fusion proteins of the present invention are included a variety of disease conditions caused by specific human cells that may be eliminated by the toxic action of the protein. One preferred application is the treatment of cancer, such as by the use of TGFα as the ligand binding agent or of autoimmune conditions such as graft-versus-host disease, organ transplant rejection, type I diabetes, multiple sclerosis, rheumatoid arthritis, systemic lupus erythematosus, myasthenia gravis and the like caused by T and B cells. The fusion proteins may also be used in vitro, for example, in the elimination of harmful cells from bone marrow before transplant. The ligand binding agent portion of the fusion protein is chosen according to the intended use. Proteins on the membranes of T cells that may serve as targets for the binding agent include CD2 (T11), CD3, CD4 and CD8. Proteins found predominantly on B cells that might serve as targets include CD10 (CALLA antigen), CD19 and CD20. CD45 is a possible target that occurs broadly on lymphoid cells. These and other possible target lymphocyte antigens for the binding agent are described in Leucocyte Typing III, A. J. McMichael, ed., Oxford University Press, 1987. Antigens found on cancer cells that may serve as targets for the binding agent include carcinoembryonic antigen (CEA), the transferrin receptor, P-glycoprotein, c-erbB2, and antigens described in the Abstracts of the Third International Conference on Monoclonal Antibody Immunoconjugates for Cancer (San Diego, Calif. 1988). Those skilled in the art will realize that ligand binding agents may be chosen that bind to receptors expressed on still other types of cells as described above, for example, membrane glycoproteins or growth factor or hormone receptors such as epidermal growth factor receptor and the like.

The PE molecules described here, and best exemplified by PE37 and PE35 described below, will also serve as signal sequences in gene therapy applications or other applications where signal sequences find use, such as with the use of vaccines. In such applications, a substantial deletion of domain III of the PE molecule could be replaced with a desired antigen. What is meant by "a substantial deletion of domain III" is a deletion of a major portion of the domain such that the function of that domain has been inactivated or destroyed. Retention of about amino acids 604–613 of domain III in the molecule is highly desired.

For example, to make a vaccine to treat AIDS or cancer a portion of a desired protein could be inserted in the place of domain III and a ligand inserted between the desired protein and the carboxyl end of PE to cause the recombinant protein to bind to an antigen presenting cell. For gene therapy a DNA sequence could be inserted in the place of domain III.

ADDITIONAL GENERAL DEFINITIONS

"Recombinant" means that the subject product is the result of the manipulation of genes into new or non-native combinations.

A "vector" is a sequence of DNA, typically in plasmid or viral form, which is capable of replicating in a host. A vector can be used to transport or manipulate DNA sequences. An "expression vector" includes vectors which are capable of expressing DNA sequences contained therein, producing a protein product. The coding sequences are linked to other sequences capable of effecting their expression, such as promoters and enhancers.

The term "without significant cytotoxicity" means that the fusion protein of the present-invention does not affect the function of the untargeted cells to any appreciable degree or to any abnormal level.

The following examples are offered by way of illustration and are not to be construed as limiting the invention as claimed in any way.

EXAMPLES

I. Construction of 37 kD Carboxyl—Terminal PE Fragment
   A. Materials
   Restriction endonucleases and DNA ligases were obtained from New England Biolabs (Beverly, Mass.), Bethesda Research Laboratories (Gaithersburg, Md.), or Boehringer Mannheim (Indianapolis, Ind.). PE(4E)/TGFα (also sometimes designated $PE^{4E}$-TGFα) was a gift from R. Kreitman, see Kreitman et al., *Bioconjugate Chem.* 3:58–62 (1992) and Krietman et al., *Bioconjugate Chem.* 3:63–68 (1992), both of which are incorporated by reference and both of which are referred to herein as "Kreitman et al.". It contains full length PE with a mutated and inactive native binding domain where amino acids 57, 246, 247 and 249 are all replaced by glutamates, TGFα placed after amino acid 607, and a proper carboxyl end of PE recreated by placing amino acids 604–613 of PE after TGFα as described in Kreitman, et al., supra.

HUT 102 cells were a gift from T. Waldmann, Leonard et al., *Nature* 300:267–269 (1982). All other cell lines were from the American Type Culture Collection (Rockville, Md.).

B. Amplification

Oligonucleotides C1, C2, C7 and C8 are detailed in Table 1 and were constructed using a DNA synthesizer (Applied Biosystems, Inc., Foster City, Calif.). Polymerase chain reaction (PCR) reactions were carried out using 10 ng pCT4 (see below) as template and reagents as per the manufacturer's instruction (Gene Amp; Perkin-Elmer Cetus Instruments, Norwalk, Conn.) in the presence of 5% formamide (Fluka Chemika, Rankokoma, N.Y.) and 100 pmol of primers C1 and C2 or C7 and C2 or C8 and C2. Each PCR reaction totaled 30 cycles consisting of denaturation at 94° C. for 1 minute, annealing at 42° C. for 90 seconds and polymerization at 72° C. for 2 minutes with a 10 second extension in each cycle. The amplified fragments were purified on 1.5% low-melting-point agarose (SeaPlaque; FMC Corp., Rockland, Me.).

derivative of PE40, NLysPE40, containing an extra lysine at the amino end, was propagated in the HB101 strain. Plasmid MS8 was prepared by ligating an oligonucleotide duplex to plasmid pVC8f(+)T (Chaudhary et al., *Proc. Natl. Acad. Sci., USA* 85:2939–2943 (1988) incorporated by reference) linearized with Nde I restriction endonuclease. The sequence of the linker was S5 found on Table 1. The sequence was confirmed by DNA sequencing (Sequenase, U.S. Biochemical, Cleveland, Ohio) in the manner described by Sanger, et al., *Proc. Natl. Acad. Sci. USA* 75:2659–2663 (1977), incorporated by reference herein. The plasmid DF1 encodes a 37 kD protein termed PE37 that contains an initial methionine followed by amino acids 281–613 of native PE. The cysteine at position 287 was replaced by serine. Plasmid DF1 was deposited with the American Type Culture Collection at Rockville, Md. on Jun. 12, 1992 and has been designated ATCC No. 69019. Plasmid CT4 (pCT4) was made by ligating a DNA fragment identical to a 551 bp (base pair) BamH1-EcoR1 fragment of plasmid 4735/4E with a 3.6 kb BamH1-EcoR1 dephosphorylated fragment of plasmid DF1. Plasmid CT4 encodes a protein termed PE37/TGFα (PE 280–613/TGFα).

PE37 deletion mutants were created by the insertion of NdeI-SacII digested PCR fragments into NdeI-SacII restriction sites found in plasmid DF1. Plasmid CT2 encodes a

TABLE 1

Linker sequence and Oligonucleotides used in PCR or to generate oligonucleotide duplexes C1: 5'-ATG TGG GAA CAA CTC GAG CAT ATG GGC TAT CCG GTG CAG C-3'
(Seq. ID No. 2)

C2: 5'-GGG CAC CGT TGC GGA TCC GGC CGC GTG CGT-3'
(Seq. ID No. 3)

C7: 5'-GAT ATA CAA ATG CAT ATG CAA CTC GAG CAG AGC GGC TAT CCG GTG-3'
(Seq. ID No. 4)

C8: 5'-CAA ATG TGG GAA CAT ATG GAG CAG AGC GGC TAT CCG GTG-3'
(Seq. ID No. 5)

C9: 5'-GAA GGA GAT ATA CAT ATG TGG GAA CAA GAG CAG TGC GG-3'
(Seq. ID No. 6)

S1: 5'-TAT GTG GGA ACA ACT CGA GCA GAG CGG CTA TCC GGT GCA GCG ACT AGT
AGC GCT CTA CCT GGC GGC GCG GCT GTC GTG GAA CCA GG-3'
(Seq. ID No. 7)

S2: 5'-TCG ACC TGG TCC CAC GAC AGC CGC GCC AGG TAG AGC GCT ACT AGT CGC
TGC ACC GGA TAG CCG CTC TCG AGT TGT TCC CAC C-3'
(Seq. ID No. 8)

S3: 5'-TCG ACC AGG TGA TCC GCG GCC-3'
(Seq. ID No. 9)

S4: 5'-GGT CCA CTA GGC G-3'
(Seq. ID No. 10)

S5: 5' TAT GCT GCA GGG TAC CAA GCT 3'
3'   A CGA CGT CCC ATG GTT CGATT 5'
(Seq. ID No.11)

C. Bacterial Strains and Plasmids

*E. coli* strain HB101 was used for the propagation of the plasmids. *E. coli* strain BL21 (λDE3), which carries an inducible T7 RNA polymerase gene on a prophage (Studier & Moffatt, *J. Mol. Biol.* 189:113–130 (1986)), was used as the host for fusion protein expression. The plasmid 4735/4E has been described previously, (Kreitman, et al., supra). It contains the gene encoding TGFα inserted after amino acid 607. Plasmid DF1 was created by insertion of the annealed oligonucleotide S1 and S2 (Table 1) into a 4.2 kb (kilobase), NdeI-SalI fragment of plasmid MS8 which encodes a methionine at position 282 and amino acids 283–613 of native PE, except a serine at position 287. Plasmid CT3 encodes a methionine at position 284 and amino acids 285-613 of native PE, except a serine at position 287. Plasmid CT14 encodes a methionine at position 287 and amino acids 288–613 of native PE. Plasmid CT8, containing an internal deletion of amino acids 314–380 from PE37, was made by the insertion of the annealed oligonucleotides S3 and S4 (Table 1) into a 3.9 kb SalI-ApaI fragment of plasmid DF1. The sequences of all four plasmids were confirmed by DNA sequencing. All mutant plasmids were restricted with BamH1 and EcoR1 and ligated to a DNA fragment identical to a 551 bp BamH1-EcoR1 fragment of plasmid VC4735/4E to create the mutant plasmids CT2/T, pCT3/T, pCT14/T and pCT8/T. These plasmids were verified by restriction analyses, and encode proteins PE282-613/TGFα, PE284-613/TGFα, PE287-613/TGFα and PE37Δ314-380/TGFα, respectively (FIG. 1).

D. Expression and Purification of Recombinant Fusion Proteins

Expression of Pseudomonas exotoxin containing fusion proteins was done using the host *E. coli* strain BL21 (λDE3) as described previously (Siegall, et al., *Proc. Natl. Acad. Sci. USA* 85:9738–9742 (1988); Chaudhary, et al., *Proc. Natl. Acad. Sci. USA* 84:4538–4542 (1987); and Chaudhary, et al, *Proc. Natl. Acad. Sci. USA* 85:2939–2943 (1988), all incorporated by reference. Cells were incubated for 90 minutes following induction with IPTG (isopropylthiogalactoside). The periplasm fraction was prepared for the mutant proteins from plasmid DF1. For proteins containing the TGFα domain, fusion proteins were purified from inclusion bodies as described in Kreitman, et al., supra.

Periplasm or inclusion bodies extracted with guanidine and renatured by rapid dilution into PBS were purified by sequential use of Q sepharose, Mono Q HR 5/5 (Pharmacia-LKB, Inc., Piscataway, N.J.) or Porous A/F (Perceptive Biosystems, Cambridge, Mass.), and TSK-250 columns using a Pharmacia LKB Biotechnology, Inc. (Piscataway, N.J.) FPLC. SDS-PAGE, as described in Laemmli, *Nature* 227:680–685 (1970), incorporated by reference, was used to analyze column fractions. The identity of PE containing proteins was verified by immunoblotting using polyclonal rabbit anti-PE antisera and a Vectastain kit (Vector Labs, Burlingame, Calif.).

E. Protein Synthesis Inhibition Assay

Inhibition of protein synthesis was carried out as described in Prior, et al., *Cell* 64:1017–1023 (1991), incorporated by reference. Cells were plated 24 hours prior to toxin addition at 15,000 cells per well in 96 well plates. Toxins or controls, diluted in 0.2% BSA-PBS (bovine serum albumin—phosphate buffered saline), were added to a final volume of 200 μl/well. After incubation at 37° C. for 16–20 hours, each well was pulsed for 2 hours with [$^3$H]-leucine (Amersham Corp., Arlington Heights, Ill.; 1 μCi diluted to 10 μl in 0.2% BSA-PBS). After freezing, the cells were harvested on glass fiber filters and the incorporation of radioactivity into protein quantitated by a Betaplate scintillation counter (Pharmacia, LKB). Results were calculated as a percentage of incorporated cpm (counts per minute) of cells incubated without toxin. Competition assays were done using toxin added to cells in the presence of 2 μg/ml of EGF.

F. ADP-Ribosylation Assay

ADP-ribosylation activity of protein samples was measured by the procedure of Collier and Kandel using wheat germ extract enriched in elongation factor 2, *J. Biol. Chem.* 246:1496–1503 (1971), incorporated by reference.

G. [$^{125}$I]-EGF Displacement Studies

A431 cells (human epidermoid cancer cells) were plated at 8,000 cells per well in 1 ml of media in 24 well plates. After 24 hours, the cells were washed twice with binding buffer (DMEM containing 50 mM MES pH 6.8 and BSA 1 mg/ml) and treated with 200 μl of binding buffer containing 0.5 ng (0.05 μCi)) of [$^{125}$I]-EGF (New England Nuclear, Inc., Boston, Mass.) combined with either 0, 0.8, 4, 20, or 100 pmol of toxin. After equilibration for 90 minutes on a rocker at 4° C., the cells were washed with binding buffer, lysed with 10 mM Tris-HCl pH 7.4 containing 0.5% SDS and 1 mM EDTA, and bound ligand counted with a gamma detector.

H. Design of a 37 kD Carboxyl-Terminal Fragment

To determine whether the 37 kD carboxyl-terminal fragment of PE (PE37) can be translocated to the cytosol and arrest protein synthesis, we constructed plasmid DF1 which encodes a protein beginning with a methionine at position 280, instead of glycine, followed by amino acids 281–613 of native PE. In native PE, replacement of gly 280 by methionine does not reduce cytotoxicity. In addition cysteine 287 was changed to a serine to reduce the number of incorrect disulfide bonds. As a result, PE37 has only 2 cysteine residues, located in domain Ib at positions 372 and 379. DNA sequencing of plasmid DF1 confirmed that it had the desired sequence. Using the T7 promoter present in plasmid DF1, PE37 was expressed in BL21 (λDE3) and found to be equally distributed between the periplasm and spheroplasts when cell fractions were analyzed by SDS-PAGE. Toxin was purified from periplasm to >90% homogeneity using anion exchange chromatography and gel filtration. The purified protein had the expected molecular weight on SDS-PAGE (37 kD) and was immunoreactive with anti-PE antibodies (FIGS. 2 and 3). Protein sequencing confirmed the 14 amino-terminal amino acids (MWEQLEQSGYPVQR). ADP ribosylation activity was identical to that of PE40, a molecule with ADP-ribosylation activity identical to native PE. See, Kondo, et al., *J. Biol. Chem.* 263:9470–9475 (1988). When tested on a number of cell lines, PE37 had very little cytotoxic activity because it could not bind to the target cells.

I. Design and activity of PE37/TGFα

To target PE37 to cells without modifying its amino-terminus, a plasmid was constructed in which a cDNA encoding TGFα was inserted so that TGFα was placed after amino acid 607 of PE37 and a carboxyl end of PE was recreated by placing amino acids (604–613) of PE after TGFA. Toxin molecules with TGFα inserted at this position and also containing an inactive cell binding domain, PE(4E)/TGFα, (also known as PE66$^{4Glu}$-TGFα) are very cytotoxic to EGF receptor bearing cells. See Kreitman, et al. supra.

The fusion protein PE37/TGFα, whose structure is shown in FIG. 1, was expressed in BL21 (λDE3) and found almost exclusively in inclusion bodies. The protein was solubilized in 7M guanidine, renatured in phosphate buffered saline, and purified to >90% homogeneity on anion exchange and gel filtration columns as described previously for other TGFα containing recombinant proteins, Kreitman, et al., supra. The purified protein migrated with the expected molecular weight (43 kD) on SDS-PAGE, was immunoreactive with antibodies against PE (FIGS. 2 and 3), and had full ADP ribosylation activity when compared with other PE molecules, Table 2. The recombinant protein was cytotoxic to cell lines expressing various numbers of EGF receptors and the cytotoxic effect was related to the number of receptors present (Table 3). Furthermore, HUT 102 cells, which do not have EGF receptors, were resistant to the toxic effects of PE37/TGFα. Cytotoxicity on A431 human epidermoid cancer cells was completely inhibited using excess EGF, indicating that PE37/TGFα was binding specifically via the EGF receptor. The $ID_{50}$ of PE37/TGFα on A431 cells was less than PE(4E)/TGFα, a molecule that contains all of domain II, and therefore must be processed prior to translocating to the cytosol (FIG. 4). This data indicates PE37/TGFα is a very active and specific recombinant toxin.

TABLE 2

Comparison of activities of various PE mutants

| Construct[1] | Plasmid | ADP Rib. (%) | $ID_{50}$[2] (A431) ng/ml | [nM] displaces $^{125}$I-EGF | Corrected cytotoxicity Index[3] |
|---|---|---|---|---|---|
| PE37 | pDF1 | 100 | 250 | ND | ND |
| PE37/TGFα | pCT4/T | 100 | 0.02 | 20 | 1000 |
| PE282-613/TGFα | pCT2/T | 100 | 0.5 | 41 | 82 |
| PE284-613/TGFα | pCT3/T | 100 | 0.25 | 14 | 56 |
| PE287-613/TGFα | pCT14/T | 100 | 2 | 12 | 6 |
| PE37Δ314-380/TGFα | pCT8/T | 100 | 25 | 8 | 0.32 |
| PE(4E)/TGFα | pVC4735/4E | 100 | 0.3 | 12 | 40 |
| PE35/TGFα | | | 0.06 | 20 | 333 |
| PE35/TGFα & KDEL | | | 0.006 | 9 | 1500 |
| TP40 (ala 265, 287, 372, 379) | | | 0.4 | 2 | 5 |
| PE37/TGFα (ser 287) | | | 0.06 | 20 | 333 |
| PE37/TGFα (cys 287) | | | 0.09 | 10 | 111 |

1. The first seven constructs represent results from one trial and the last five constructs represent results from a second and different trial. PE37/TGFα (ser287) = PE37/TGFα
2. $ID_{50}$ is determined by the concentration of toxin that inhibits protein synthesis in A431 cells by 50% as measured by incorporation of $^3$H-leucine.
3. The cytotoxicity index was determined by dividing the concentration of toxin necessary to displace 50% of the bound $^{125}$I-EGF by the $ID_{50}$ of the toxin. A larger number for this index indicates a more desirable compound.

TABLE 3

Activity of PE37/TGFα on malignant cell lines with varying numbers of EGF receptors

| Cell line | Type | Receptor number (sites/cell) | $ID_{50}$ (ng/ml) |
|---|---|---|---|
| A431 | Epidermoid | $2 \times 10^6$ | 0.02 |
| HT29 | Colon | $1 \times 10^5$ | 1 |
| MCF7 | Breast | $1 \times 10^4$ | 3 |
| HUT 102 | Leukemic | 0 | >1000 |

J. Mutants of PE37/TGFα

An examination of the amino terminal portion of PE37/TGFα reveals that the 37 kD fragment of PE contains seven amino-terminal amino acids (MWEQLEQ) that form a negatively charged leader sequence that leads into the B alpha helix (aa 287–308). To determine whether the amino-terminus of PE37 was necessary for activity, a series of deletion mutants were constructed in which two, four or seven amino acids were deleted from the amino terminus (FIG. 1 and Table 1). A fourth mutant was constructed which contained a normal amino terminus but a large internal deletion (amino acids 314–380). To be able to test for cytotoxicity on cell lines containing EGF receptors, TGFA was placed near the carboxyl terminus of all of these recombinant proteins (FIG. 1).

All mutant proteins containing TGFA were expressed as inclusion bodies in BL21 (λDE3) and purified as described. Mutant proteins were purified to >90% homogeneity, migrated with appropriate molecular weights on SDS-PAGE, were immunoreactive to rabbit anti-PE antibodies (FIGS. 2 and 3) and had full ADP ribosylation activity (Table 2). $ID_{50}$'s on A431 and MCF7 cells are detailed in Table 2 and FIGS. 4 and 5. PE37/TGFα (PE 280-613/TGFα) was the most active molecule with deletion of two or four amino-terminal amino acids decreasing activity by 12- to 25-fold. Deletion of seven terminal amino acids decreased activity further and the internal deletion resulted in a large loss of cytotoxicity.

A decrease in cytotoxicity may be attributed to decreased binding of the recombinant toxin to the EGF receptor. Because TGFA has three disulfide bonds, a variety of improperly folded forms can be generated during the refolding process, Kreitman, supra. To determine whether differences in EGF receptor binding contributed to differences in $ID_{50}$'s between PE37/TGFα and the other recombinant toxins, an [$^{125}$I]-EGF displacement assay was conducted (FIG. 6). Each toxin's cytotoxic activity was then corrected for differences in EGF receptor binding. A corrected cytotoxicity index value was calculated by dividing the concentration of toxin (nM) that displaced 50% of [$^{125}$I]-EGF from EGF receptors by the $ID_{50}$ of the recombinant toxin on A431 cells (Table 2). This index highlights the superior cytotoxic activity of PE37/TGFα compared to the other mutants described here and to PE(4E)/TGFα.

The 37 kD protein (termed PE37) described above is a preferred embodiment. Because the amino-terminal methionine is at amino acid position 280, this molecule should not require either proteolysis or disulfide bond reduction to enable it to translocate to the cytosol. Substitution of methionine for glycine at position 280 does not decrease cytotoxicity. To target PE37, a chimeric molecule was created using a cDNA encoding TGFA. PE37/TGFα acted specifically to kill target cells because cytotoxicity was inhibited by excess EGF, while HUT 102 cells, which lack EGF receptors, were insensitive to PE37/TGFα. Amino acids 253–280 are apparently necessary for toxin function only to facilitate proteolytic processing.

Analysis of the metabolism of PE by target cells has shown that about 10% of cell-bound PE molecules are processed. See, Ogata, et al., *J. Biol. Chem.* 265:20678–20685 (1990). This indicates that proteolytic processing may be a rate-limiting step in the action of PE. Table 2 suggests that bound PE37/TGFα is over 20-fold more efficient than bound PE(4E)/TGFα reaching the cytosol. Since the fragment of PE(4E)/TGFα that translocates is almost identical to PE37/TGFα, the actual membrane translocation step is similar for both molecules. Thus, it is very likely that proteolytic processing limits the cytotoxicity of PE(4E)/TGFα.

Previous studies (Siegall et al., *Biochem* 30:7154–7159 (1991)) indicate that amino acids 346–380 can be deleted from PE without any loss of activity but additional mutations at position 345 are deleterious. The poor activity of the PE37/TGFα mutant lacking residues 314–380 indicates that residues between 314–346 are involved in translocation. This requirement is independent of the need to generate the 37 kD active fragment. Thus, the portion of domain II that is important for translocation appears to be the 66 amino acid residues at positions 280–345. Domain Ib and III (amino acids 364–613) are also not necessary for translocation because they can be replaced with the ribonuclease barnase to generate a cytotoxic molecule, as described in Prior, et al., *Biochemistry* 31:3555–3559 (1992).

The presence of the amino-terminal leader sequence (MWEQLEQ) (Seq. ID No. 13) that leads into the B helix (amino acids 287–308) of PE37/TGFα is important for full cytotoxic activity. Mutant proteins with deletion of 2, 4 or 7 amino acids from the amino end of PE37/TGFα were less active than PE37/TGFα. When corrected for binding to the EGF receptor, a 12- to 25-fold loss of cytotoxic activity was observed in the mutants lacking two or four of the amino-terminal amino acids. These amino-terminal deletion mutants each retain one glutamine and a net negative charge. A further ten-fold decrease in corrected cytotoxicity was seen with a seven amino acid deletion.

II. Construction of 35 kD Carboxyl-Terminal PE Fragment and Antibody-PE Fusion Protein.

A. Materials and Cell Lines

Unless otherwise specified to the contrary, the material and cell lines were obtained from the same sources described under the previous example.

B. Amplification

Oligonucleotides C9 and C2 (see Table 1) were constructed as described above using a DNA synthesizer (Applied Biosystems). Polymerase chain reaction (PCR) was carried out using 10 ng of plasmid DF1 (described above) as template and reagents as per the manufacturer's instructions (Gene Amp; Perkin-Elmer/Cetus) in the presence of 5% formamide (Fluka Chemika) and 100 pmol of primers C9 and C2. Each PCR reaction totalled 30 cycles consisting of denaturation at 94° C. for 1 minute, annealing at 42° C. for 90 seconds and polymerization at 72° C. for 2 minutes with a 10 second extension in each cycle. The amplified fragments were purified on 1.5% low-melting-point agarose (SeaPlaque, FMC).

C. Bacterial Strains and Plasmids

HB101, described above, was used for the propagation of the plasmids. BL21 (λDE3), which carries an inducible T7 RNA polymerase gene on a prophage, also described above, was used as the host for fusion protein expression. Plasmid CT132 was made by the insertion of a NdeI-SacII digested PCR fragment (amplified using C9 and C2) into a dephosphorylated 3.6 kb NdeI-SacII fragment of plasmid DF1, described above. Plasmid CT11 was created by ligating a 515 bp SalI-BamH1 fragment of a plasmid containing a DNA sequence identical to plasmid CS10 (Siegall et al., *Biochem.* 30:7154–59 (1991)) which encodes a PE mutant containing a deletion of amino acids 365–380 from domain Ib, with a 3.7 kb SalI-BamH1 dephosphorylated fragment of plasmid CT132. Plasmid CT11 was verified by DNA sequencing and encodes a protein termed PE35 that consists of a methionine and amino acids 281–364,381–613 of native PE.

D. Expression and Purification of Recombinant Fusion Proteins

Expression of Pseudomonas exotoxin mutant proteins was done using the host BL21 (λDE3) as described under the previous example. Cells were incubated for 90 minutes following induction with IPTG. The periplasm fraction was prepared for PE35 and NlysPE38 purification. NlysPE38 is a mutant PE protein that contains aa 253–364,381–613 of PE preceded by an 11 amino acid peptide containing a lysine residue that is easily derivatized. NlysPE38 was purified by sequential use of Q sepharose, Mono Q (HR 5/5; Pharmacia) and TSK-250 (Tosohaas, Montgomeryville, Pa.) columns using Pharmacia LKB Biotechnology Inc. FPLC as described in the prior example. Periplasm containing PE35 was purified by elution from Q sepharose at 0.26–0.30M NaCl in 20 mM Tris pH 7.4. The eluant was injected onto a chelating sepharose column (Pharmacia) that had been 50% saturated with 1 mg/ml $CuSO_4$ in 50 mM Tris-acetate pH 7.0 containing 1M NaCl. The flow through contained almost pure PE35 that was purified as monomer on a TSK-250 column in PBS containing 10 mM EDTA and 10 mM DTT.

SDS-PAGE using the method of Laemmli, supra, was used to analyze column fractions. The identity of PE containing proteins was verified by immunoblotting using rabbit sera reactive with PE. Counter antibody and substrate were provided using a Vecta kit (Vector Labs). Mutant PE protein concentrations were determined by absorbance at 280 nm, assuming an extinction coefficient of 1.2 ml/mg-cm.

E. Construction of Immunotoxins

NlysPE38 (6–13 mg/ml) in 0.2M sodium phosphate (pH 8.0) containing 1 mM EDTA was derivatized with a 5-fold molar excess of iminothiolane and incubated at 37° C. for 30 minutes. Protein was separated from unreacted cross-linker on Sephadex G-25 (PD10; Pharmacia). Derivatization typically introduced 0.5 moles of thiol per mole of NlysPE38 as measured using Ellman's reagent (Ellman, *Arch. Biochem. Biophys.* 82:70–77 (1959). As well, NlysPE38 (6–13 mg/ml) in 0.2M sodium phosphate (pH=7) containing 1 mM EDTA was derivatized with a 3-fold molar excess of SMCC (succinimidyl 4-(N-maleimidomethyl) cyclohexane-1-carboxylate) and incubated at 22° C. for 1 hour (Yoshitake, et al., *J. Biochem.* 92:1413–1424 (1982). Protein was separated from reactant on Sephadex G-25. Derivatization typically introduced 0.5 reactive groups per mole of NlysPE38. PE35 was stored in 0.2M sodium phosphate (pH 7.0) containing 1 mM EDTA and 50 mM DTT and separated from DTT on Sephadex G-25 prior to coupling to antibody. Monoclonal antibody (MAb) B3 is reactive against polysaccharide antigen found on many human tumors and was purified from serum free culture medium as described. Pastan, et al., *Cancer Res.* 51:3781–7 (1991), incorporated by reference herein. MAb HB21 is directed against the human transferrin receptor and was purified from the ascities of nude mice bearing HB21 as described. MAb concentrations were determined by absorbance at 280 nm, assuming an extinction coefficient of 1.4 ml/mg-cm. B3 and HB21 (4–8 mg/ml) in 0.2M sodium phosphate (pH 7.0) containing 1 mM EDTA were reacted with a two-fold and four-fold molar excess of SMCC, respectively, and incubated at 22° C. for one hour. Derivatized MAb was separated from reactant using Sephadex G-25. B3 and HB21 had 0.83 and 1.0 reactive groups measured per molecule, respectively, under these conditions. See Yoshitake, et al., supra. B3 and HB21 (4–5 mg/ml) in 0.2M sodium phosphate (pH 8.0) containing 1 mM EDTA were also reacted with a two-fold or three-fold molar excess of SPDP, respectively, and incubated at 22° C. for 30 minutes. Derivatized MAb was separated from reactant using Sephadex G-25. B3 and HB21 had 0.79 and 0.56 reactive groups measured per molecule, respectively, under these conditions. (Carlsson, et al., *Biochem. J.* 173:723–737 (1978).) B3 or HB21 derivatized with either SPDP or SMCC were each separated into two pools and reacted with a 2 to 3 molar excess of NlysPE38 that had been derivatized with iminothiolane or with reduced PE35 for 16 hours at 222° C. Reactions were terminated by the addition of iodoacetamide (Sigma Chemical Co., St. Louis, Mo.) to a 1 mM final concentration. In addition, B3 was derivatized using iminothiolane. B3 (5–10 mg/ml) in 0.2M sodium phosphate (pH 8.0) was reacted with a two molar excess of iminothiolane at 37° C. for one hour. Derivatized antibody was separated from reactant using Sephadex G-25. B3 had 1.0 reactive groups introduced under these conditions (Ellman, supra).

The MAb was mixed with PE35 that that had been derivatized with DTNB (5,5'-dithio-bis-(2-nitrobenzoic acid)) as described (FitzGerald, *Meth. Enzymol.* 151:139–145 (1987)). After a two hour incubation at 22° C., reactions were terminated by the addition of cysteine (Pierce) to a 0.2 mM final concentration. As well, B3 derivatized with iminothiolane was reacted for 2 hours at 22° C. with NlysPE38 that had been derivatized with SMCC. The reaction was terminated with 1 mM iodoacetamide. Immunotoxins were purified as single peaks by sequential use of Mono Q (HR 5/5) and TSK-250 columns using FPLC.

F. ADP-Ribosylation Assay

ADP-ribosylation activity of protein samples was measured by the procedure of Collier and Kandel using wheat germ extract enriched in elongation factor 2, as described in the previous example.

G. Protein Synthesis Inhibition Assay

Inhibition of protein synthesis was carried out as described in the previous example. Cells were plated 24 hours prior to toxin addition at 15,000 cells per well in 96 well plates. Toxins or controls, diluted in 0.2% BSA-PBS, were added to a final volume of 200 μl/well. After incubation at 37° C. for 20 hours, each well was pulsed for 2 hours with [$^3$H]-leucine (1 μCi diluted to 10 μl in 0.2% BSA-PBS; Amersham). After freezing and thawing, the cells were harvested on glass fiber filters and the incorporation of radioactivity into protein quantitated by a Betaplate (Pharmacia, LKB) scintillation counter. Results were calculated as a percentage of incorporated cpm of cells incubated without toxin. Competition assays were done using immunotoxin added to cells in the presence of the respective MAb. All assays were performed in triplicate and values were averaged.

H. Design of a 35 kD Carboxyl-Terminal Fragment

We sought to determine whether a 35 kD carboxyl-terminal fragment of PE (termed PE35) could be conjugated to monoclonal antibodies to create potent immunotoxins. A plasmid encoding PE35 was constructed using plasmid CT132.

Figure 9:
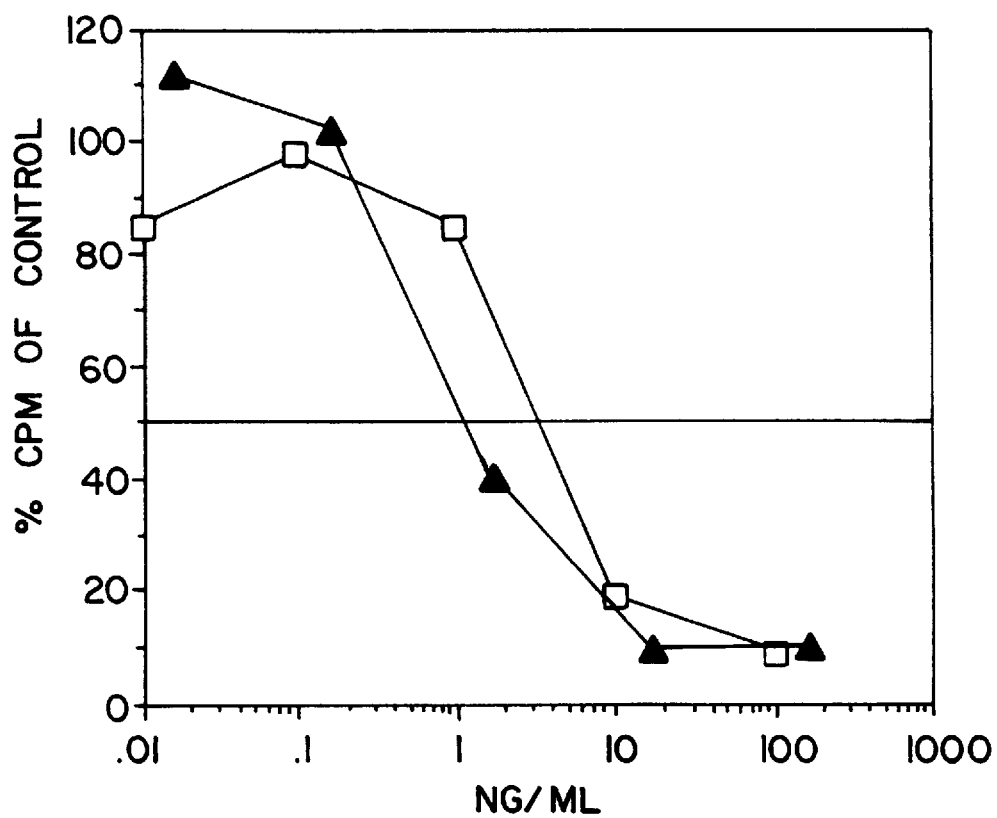
FIG. 9: Protein inhibition activity of B3 conjugates on MCF7 cells: B3-S-C-PE38(open square) and B3-S-S-PE35 (closed triangle). Both immunotoxins were constructed by derivatizing MAb with iminothiolane.

Plasmid CT132 was constructed using a PCR fragment that reintroduces a cysteine at position 287 of PE37. DNA sequencing confirmed that this mutation was present. Plasmid CT11 was constructed by replacing PE encoding DNA sequences of plasmid CT132 with a PE encoding DNA sequence containing a deletion of amino acids 365–380 from domain Ib. This deletion does not affect the cytotoxicity of PE proteins. Thus, plasmid CT11 (f+T) contains a T7 promoter and DNA encoding a met at position 280 followed by amino acids 281–364,381–613 of native PE. The protein encoded by this plasmid (PE35) has a single cysteine residue at position 287 (FIG. 7). PE35 was expressed in BL21 (λDE3) and found to be equally distributed between the periplasm and spheroplast on SDS-PAGE. Purification from periplasm to >95% homogeneity was done using anion exchange and chelation chromatography and gel filtration. PE35 was found to be of expected molecular weight on SDS-PAGE (35 kD) and was immunoreactive with rabbit sera reactive with PE. ADP ribosylation activity was identical to that of lysPE40 (Collier & Kandel, supra), a molecule with ADP-ribosylation activity identical to native PE. The number of thiol groups was found to be one per mole when measured using Ellman's reagent. When tested on a number of cell lines, PE35 had very little cytotoxic activity because it could not bind specifically to target cells (Table 4).

I. Design and Activity of Immunotoxins Using HB21

To determine whether PE35 could be specifically targeted to cells it was conjugated to the MAb HB21 (ATCC), an antibody that recognizes the human transferrin receptor. PE35 was coupled using both a thioether and disulfide bond.

To compare the activity of PE35 based immunotoxins with previously made molecules, NlysPE38, a molecule that contains amino acids 253–364,381–613 of PE preceded by an 11-amino acid peptide that contains an accessible lysine residue (FIG. 7), was derivatized with iminothiolane to create a free sulfhydryl group, and was coupled to MAb derivatized with either SMCC (to produce a thioether bond) or SPDP (to produce a disulfide bond). Each of the four immunotoxins were purified to >95% homogeneity using anion exchange chromatography and gel filtration. They each migrated with a molecular weight of 190,000 kD indicating a one-to-one ratio of antibody and toxin. Reducing SDS-PAGE produced the expected pattern of antibody and toxin fragments. When HB21 conjugated to PE35 through a thioether bond (HB21-S-C-PE35) was reduced and subjected to PAGE, it produced the MAb heavy chain (50 kD) and MAb light chain (20 kD) as well as heavy and light chains bound to PE35 (corresponding to the higher molecular weight bands on the gel). When HB21 conjugated through a thioether bond to NlysPE38 was analyzed in a similar manner, it resulted in heavy and light chains as well as heavy and light chains bound to NlysPE38. HB21 conjugated to NlysPE38 through a disulfide bond (HB21-S-S-PE38) reduced to produce MAb heavy and light chains as well as free toxin (38 kD). Similarly, HB21 conjugated to PE35 through a disulfide bond (HB21-S-S-PE 35) reduced to produce MAb heavy and light chains as well as free toxin (35 kD). Western blotting of reduced immunotoxins, using polyclonal rabbit sera reactive with PE, confirmed the presence of free toxin (in the case of disulfide conjugates) or toxin bound to antibody heavy and light chains (in the case of thioether conjugates).

The conjugates were then tested on A431 and MCF7 cells to determine their activities. Conjugates employing a disulfide linkage to PE35 were most active on A431 and MCF7 cells (Table 4 and FIG. 8). NlysPE38 conjugates displayed nearly identical cytotoxicity regardless of the method of conjugation, but were five-fold less active than those containing a disulfide bond to PE35 on A431 cells. The thioether conjugate made using PE35 was more than 100-fold less active than the disulfide conjugate containing PE35. Mouse L929 cells, which do not contain the human transferrin receptor were resistant to the toxic effects of immunotoxin containing HB21. Furthermore, cytotoxicity on the A431 human epidermoid cancer cell line was inhibited using 10 μg/ml of HB21, indicating that immunotoxin was binding specifically via the human transferrin receptor.

J. Design and Activity of Imunotoxins Using B3:

To determine whether PE35 could be specifically targeted to human cancer cells it was conjugated to MAb B3, a MAb that recognizes polysaccharide antigen found on many human cancers (Pastan, Cancer Res., supra). PE35 was activated with DTNB and coupled through a disulfide bond to B3 that had been derivatized with iminothiolane. For comparison, an immunotoxin made by coupling NlysPE38 (that had been derivatized with SMCC) to B3 (that had been derivatized with iminothiolane) was used. Each of the immunotoxins was purified to >95% homogeneity using anion exchange chromatography and gel filtration. They each migrated with a molecular weight of approximately 210,000 kD, indicating a one-to-one ratio of antibody and toxin. Reducing SDS-PAGE produced an expected pattern of antibody and toxin fragments. B3 conjugated to NlysPE38 through a thioether bond (B3-S-C-PE38) reduced to produce MAb heavy chain (50 kD) and light chain (20 kD) as well as MAb heavy and light chains bound to PE38. B3 conjugated to PE35 through a disulfide bond (B3-S-S-PE35) reduced to produce MAb heavy and light chain as well as free toxin (35 kD). Western blotting using polyclonal rabbit sera to PE of reduced immunotoxins confirmed the presence of free toxin (in the case of the disulfide conjugate)

or toxin bound to MAb heavy and light chain (in the case of the thioether conjugate). The immunotoxin containing a disulfide bond was twice as active on A431 cells and slightly more active on MCF7 cells (Table 4 and FIG. 9). KB cells were resistent to the toxic effects of both toxins (Table 4). KB cells are derived from a human epidermoid carcinoma and obtained from ATCC. As well, the activity of the immunotoxin on MCF7 cells was completely inhibited by 900 μg/ml of B3, indicating the immunotoxin was binding specifically to the B3 antigen.

A thioether conjugate between B3 and NlysPE38, in which MAb had been derivatized with iminothiolane and NlysPE38 had been derivatized with SMCC, was compared to a similar conjugate made using the identical proteins but reversing the derivatizing agents. Interestingly, B3 that had been derivatized with SMCC was six- to eight-fold less active than an identical immunotoxin in which B3 had been derivatized with iminothiolane. Similarly, immunotoxin containing PE35 conjugated to B3 through a disulfide bond was nine-fold less active when B3 had been derivatized with SPDP than when B3 had been derivatized with iminothiolane. A significant effect of derivatizing agents on the activity of immunotoxin containing HB21 was not observed.

PE35 retains the unique features of PE37 and can be easily conjugated to antibody. PE35 has full ADP ribosylation activity; it contains a single cysteine residue at position 287 so it can be reliably coupled to antibody through either a thioether or disulfide bond. We compared immunotoxin made using PE35 to ones constructed using NlysPE38 that had been derivatized with iminothiolane to create a free sulfhydryl group. MAb HB21 that had been derivatized with either SMCC or SPDP were each separated into two pools and reacted with each toxin in parallel to create conjugates employing either a thioether or disulfide bond, respectively. Derivatization was done to ensure a predominance of immunotoxin containing antibody and toxin in a one-to-one ratio. Only purified one-to-one immunotoxin was used for the analyses done here.

As expected, NlysPE38 conjugates made employing either a disulfide or thioether linkage to HB21 had similar toxicities. Immunotoxin containing PE38 requires two critical processing steps to liberate a carboxyl terminal fragment capable of reaching the cytosol to cause cell death, regardless of the method of conjugation—(1) proteolytic processing between amino acids 279 and 280 and (2) reduction of a disulfide bond spanning amino acids 265 and 287. In contrast, HB21 conjugated to PE35 through a disulfide bond was five-fold more active on A431 cells than PE38 conjugates. Because the portion of each immunotoxin that reaches the cytosol is similar (amino acids 280–264,381–613 of PE), proteolytic processing may be rate-limiting in the action of PE38 containing immunotoxin on these cells. HB21-S-S-PE35, however, did not exhibit increased cytotoxicity on the human breast carcinoma MCF7 cell line in comparison to conjugates containing NlysPE38. It is possible that MCF7 cells are more efficient than A431 cells at proteolyzing PE38. Hence, proteolysis of PE mutants may not be rate-limiting in these cells. The fact that PE35 and PE38 have similar non-specific toxicities on this cell line (200 ng/ml versus 300 ng/ml, respectively) reinforces the contention that MCF7 cells process NlysPE38 nearly as well as PE35.

Because PE35 does not contain the proteolytic site recognized by mammalian cells that process PE, immunotoxin containing PE35 linked to HB21 through a thioether bond were quite inactive. The small degree of activity observed may be attributed to proteolytic processing occurring at other sites within the MAb or PE35 and inefficient translocation of the resulting fragments.

Immunotoxin containing B3 conjugated to PE35 through a disulfide bond were also more active than a B3 thioether conjugate to NlysPE38. However, the magnitude of the effect of bypassing proteolytic processing was less than that observed with HB21 conjugates. Interestingly, the B3 conjugate made using SMCC to derivatize MAb was less active than the same immunotoxin made in which MAb was derivatized with iminothiolane and NlysPE38 was derivatized with SMCC. While both of these agents react with amino groups, they differ in polarity (iminothiolane>SPDP>SMCC). The nonpolar reactant SMCC derivatized a unique lysine residue and interfered with a critical binding property of B3 during the derivatization process. As well, a PE35 disulfide conjugate made using iminothiolane to derivatize B3 was 10-fold more potent than one using SPDP to derivatize B3.

K. In vivo results with B3-S-S-PE35

Figure 10:
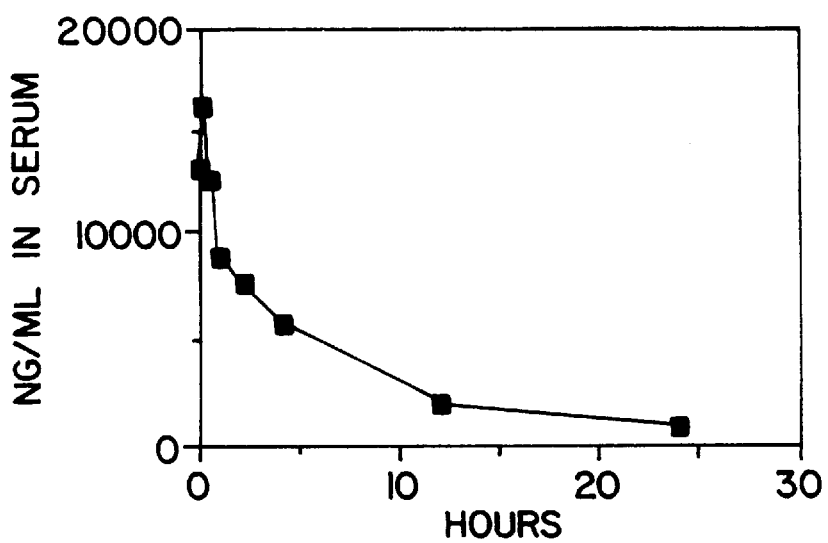
FIG. 10: Serum levels of B3-S-S-PE35 were determined after intravenous injection of 5 μg immunotoxin. The level of B3-S-S-PE35 was assayed by incubating serum with A431 cells and measuring its effects on protein synthesis. A standard curve was made with B3-S-S-PE35 diluted in control mouse serum.

B3-S-S-PE35 was injected intravenously into mice at a level of 5 μg. Serum levels of the immunotoxin were determined over a period of over 20 hours by incubating the serum with A431 cells and measuring the effect on protein synthesis as described above. A standard curve was made with B3-S-S-PE35 diluted in control mouse serum. See FIG. 10.

Figure 11:
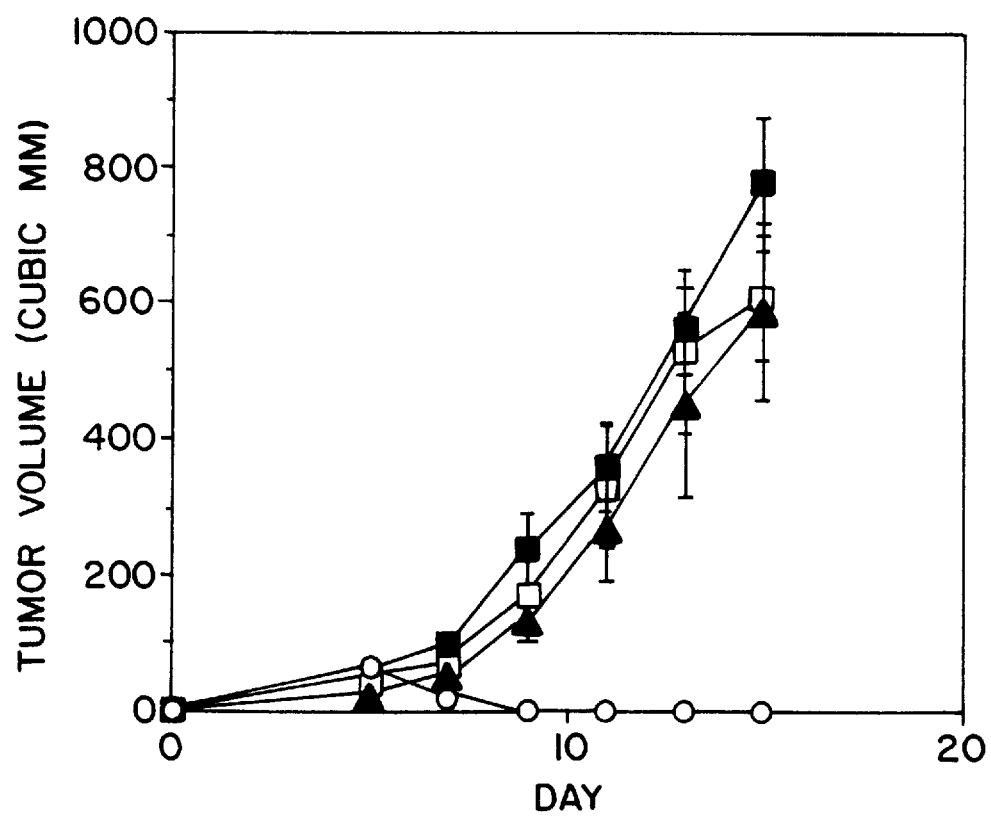
FIG. 11: Effect of B3-S-S-PE35 on the growth of subcutaneous A431 tumors in nude mice. Animals received 2,000,000 cells on day 0 and a single intravenous dose of 25 μg of B3-S-S-PE35(open circle), or an equimolar amount of B3(closed triangle) or PE35(open square) or PBS containing HSA(closed square). Bars show standard error of mean.

The effect of B3-S-S-PE35 on the growth of subcutaneous A431 tumors in nude mice was determined. The mice received 2,000,000 A431 cells on day 0 and a single intravenous dose on day 5 of 25 μg of B3-S-S-PE35, an equimolar amount of B3, PE35 or PBS containing HSA. The results over time on tumor growth measured in cubic mm are shown on FIG. 11. The immunotoxin caused complete regression of the tumor.

III. Bladder Cancer and PE35

Patients diagnosed with bladder cancer may be treated with PE35/TGFα having a carboxyl terminal sequence KDEL by instilling the protein in 60 ml of diluent once a week by catheter for a period of six weeks. This molecule is more active and smaller than TP40 and will penetrate into bladder tumors better than larger molecules and be effective.

IV. Anti-Tumor Activity Using PE35/B3(Fv)/KDEL

Patients diagnosed with tumors bearing the B3 antigen (including breast, epidermoid, gastric and prostate carcinoma cells) may be treated by administering intravenously to those patients a PE molecule comprising PE35 fusion protein with B3Fv having a carboxyl terminal sequence KDEL at a dosage of 1–100 mg per patient per day. "B3Fv" refers to a sequence including the heavy and light chain regions of MabB3 connected by a flexible linker (Gly, Ser), which starts at the carboxyl end of the heavy chain Fv domain and ends at the amino terminus of the light chain Fv domain, all as described in commonly assigned U.S. Ser. No. 07/767,331, incorporated by reference herein. This gene encoding this protein is fused to the PE35 gene.

TABLE 4

CYTOTOXIC ACTIVITIES ($ID_{50}$) OF PROTEINS AND IMMUNOTOXINS

| Toxin or Immunotoxin | A431 | MCF7 | L929 | KB |
| --- | --- | --- | --- | --- |
| PE35 | 800 | 200 | ND | ND |
| NLysPE38 | >1000 | 300 | ND | ND |
| HB21-S-C-PE35 | 200 | 30 | >1000 | ND |
| HB21-S-C-PE38 | 5 | 1.2 | >1000 | ND |
| HB21-S-S-PE38 | 5 | 2 | >1000 | ND |
| HB21-S-S-PE35 | 1 | 1.2 | >1000 | ND |
| B3-S-C-PE38 | 6 | 3.2 | ND | >1000 |
| B3-S-S-PE35 | 4.7 | 1.0 | ND | >1000 |

What is claimed is:

1. An isolated and purified recombinant Pseudomonas exotoxin (PE) fusion protein wherein a ligand binding agent is fused to a PE molecule in which domain Ia is deleted and from 1 to 28 amino acids from the amino terminal end of domain II are deleted.

2. The recombinant PE of claim 1, wherein the ligand binding agent is fused after about amino acid position 607 and is followed by amino acids 604–613 of domain III.

3. The recombinant PE of claim 1, wherein the ligand binding agent is TGFα.

4. The recombinant PE of claim 1, wherein the ligand binding agent is an antibody or binding fragment thereof.

5. The recombinant PE of claim 1, wherein the ligand binding agent is a hormone.

6. The recombinant PE of claim 1, wherein the ligand binding agent is a growth factor.

7. The recombinant PE of claim 1, wherein the ligand binding agent specifically binds a cancer cell receptor.

8. The recombinant PE of claim 1, comprising amino acids 280 to 364 and 381 to 613 of PE with TGFα inserted within the recombinant PE molecule after about amino acid 607 and followed by amino acids 604–613 of domain III.

9. The recombinant PE molecule of claim 1, wherein the PE molecule includes an endoplasmic retention sequence at a carboxyl terminal end of the molecule.

10. The recombinant PE fusion protein of claim 1, wherein the molecule further comprises a substantial deletion of domain III.

11. The recombinant fusion protein of claim 10, wherein about amino acids 604 to 613 of domain III are retained.

12. The recombinant PE fusion protein of claim 11, wherein the ligand binding agent is fused to the PE in place of deleted domain III.

13. An isolated and purified recombinant Pseudomonas exotoxin (PE) fusion protein wherein a ligand binding agent is fused to a PE molecule in which:

(a) domain Ia is deleted;

(b) from 1 to 28 amino acids from the amino terminal end of domain II are deleted; and, (c) a methionine residue is inserted at the resultant amino terminus of said molecule;

(d) wherein the fusion protein is further characterized in that it is at least twenty times more cytotoxic to target cells bound by the ligand binding agent in a cytotoxicity assay when compared with an unmodified PE40 fused to the ligand binding agent.

* * * * *